(12) United States Patent
Hyde et al.

(10) Patent No.: US 8,463,288 B2
(45) Date of Patent: Jun. 11, 2013

(54) IRRADIATION SELF-PROTECTION FROM USER TELECOMMUNICATION DEVICE

(75) Inventors: Roderick A. Hyde, Redmond, WA (US); Muriel Y. Ishikawa, Livermore, CA (US); Jordin T. Kare, Seattle, WA (US); Thomas J. Nugent, Jr., Bellevue, WA (US); Clarence T. Tegreene, Bellevue, WA (US); Thomas A. Weaver, San Mateo, CA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 399 days.

(21) Appl. No.: 12/803,143

(22) Filed: Jun. 18, 2010

(65) Prior Publication Data
US 2011/0309945 A1 Dec. 22, 2011

(51) Int. Cl.
*H04W 24/00* (2009.01)
(52) U.S. Cl.
USPC .......... 455/456.1; 340/571; 340/573.1; 340/686.6; 455/115.1; 455/575.1
(58) Field of Classification Search
USPC ............ 340/573.1, 573.4, 686.6, 539.23, 340/568.1, 571; 455/456.1, 456.6, 115.1, 455/115.3, 115.4, 572, 575.1, 575.9, 226.1, 455/226.2, 226.4
See application file for complete search history.

(56) References Cited

U.S. PATENT DOCUMENTS

| | | | |
|---|---|---|---|
| 3,764,819 A | 10/1973 | Muller | |
| 5,440,290 A | 8/1995 | McCullough et al. | |
| 5,459,405 A | 10/1995 | Wolff et al. | |
| 5,532,681 A | 7/1996 | Peters et al. | |
| 5,729,604 A | 3/1998 | Van Schyndel | |
| 5,802,445 A | 9/1998 | Wiedeman et al. | |
| 5,805,067 A | 9/1998 | Bradley et al. | |
| 5,877,630 A | 3/1999 | Kraz | |
| 5,905,262 A | 5/1999 | Spanswick | |
| 5,956,626 A | 9/1999 | Kaschke et al. | |
| 6,134,423 A | 10/2000 | Wiedeman et al. | |
| 6,272,325 B1 | 8/2001 | Wiedeman et al. | |
| 6,456,856 B1 | 9/2002 | Werling et al. | |
| 6,492,957 B2 | 12/2002 | Carillo, Jr. et al. | |
| 6,603,981 B1 | 8/2003 | Carillo, Jr. et al. | |
| 6,650,896 B1 | 11/2003 | Haymes et al. | |
| 6,674,491 B2 | 1/2004 | Tsou | |
| 6,871,139 B2 | 3/2005 | Liu et al. | |
| 6,919,845 B2 * | 7/2005 | Ozaki et al. ............ | 343/703 |

(Continued)

FOREIGN PATENT DOCUMENTS

| WO | WO 95/03549 | 2/1995 |
|---|---|---|
| WO | WO 2007/023264 A1 | 3/2007 |

OTHER PUBLICATIONS

PCT International Search Report; International App. No. PCT/US2011/001082; Sep. 29, 2011; 13 pages.

(Continued)

*Primary Examiner* — Thomas Mullen

(57) ABSTRACT

Exemplary methods, systems and components enable detection and/or monitoring and/or control of electromagnetic radiation (EMR) exposure of target body-related portions of a user operating a telecommunication device. In some embodiments a risk-assessment output is provided based on a safety threshold or predetermined intrusion level of EMR exposure.

54 Claims, 23 Drawing Sheets

U.S. PATENT DOCUMENTS

| | | | |
|---|---|---|---|
| 6,934,515 | B2 | 8/2005 | Wallach |
| 6,947,764 | B2 | 9/2005 | Carillo, Jr. et al. |
| 7,035,609 | B1 | 4/2006 | Fry |
| 7,053,629 | B2 | 5/2006 | Nevermann |
| 7,084,819 | B2 | 8/2006 | De La Torre Barreiro et al. |
| 7,088,999 | B2 | 8/2006 | Shih et al. |
| 7,113,811 | B2 | 9/2006 | Goris et al. |
| 7,117,024 | B1 | 10/2006 | Dorfman |
| 7,146,139 | B2 | 12/2006 | Nevermann |
| 7,248,995 | B2 | 7/2007 | Itsuji et al. |
| 7,319,889 | B2 | 1/2008 | Goris et al. |
| 7,417,580 | B2 | 8/2008 | Abe et al. |
| 7,467,049 | B2 | 12/2008 | Hayes et al. |
| 7,495,224 | B2 | 2/2009 | Widener et al. |
| 7,522,065 | B2 | 4/2009 | Falcon |
| 7,557,353 | B2 | 7/2009 | Black et al. |
| 7,610,027 | B2 * | 10/2009 | Alapuranen .................. 455/117 |
| 8,090,445 | B2 | 1/2012 | Ginggen |
| 2002/0016155 | A1 * | 2/2002 | Charbonnier .................. 455/550 |
| 2002/0075189 | A1 | 6/2002 | Carillo, Jr. et al. |
| 2002/0118118 | A1 | 8/2002 | Myllymaki et al. |
| 2003/0064761 | A1 | 4/2003 | Nevermann |
| 2003/0080277 | A1 | 5/2003 | Bauer, Jr. et al. |
| 2004/0039684 | A1 | 2/2004 | Sandor |
| 2004/0121795 | A1 | 6/2004 | Shih et al. |
| 2005/0103978 | A1 | 5/2005 | Yang et al. |
| 2005/0153754 | A1 | 7/2005 | Shanks et al. |
| 2005/0246088 | A1 | 11/2005 | Doherty et al. |
| 2005/0288038 | A1 | 12/2005 | Kim |
| 2006/0093161 | A1 | 5/2006 | Falcon |
| 2006/0139034 | A1 | 6/2006 | Nevermann |
| 2006/0151709 | A1 | 7/2006 | Hahl |
| 2006/0227340 | A1 | 10/2006 | Shioda et al. |
| 2007/0038402 | A1 | 2/2007 | Zhang |
| 2007/0096933 | A1 | 5/2007 | Enitan et al. |
| 2007/0106775 | A1 | 5/2007 | Wong |
| 2007/0185553 | A1 | 8/2007 | Kennedy |
| 2007/0241863 | A1 | 10/2007 | Udagawa et al. |
| 2007/0276270 | A1 | 11/2007 | Tran |
| 2008/0014872 | A1 | 1/2008 | Tucek et al. |
| 2008/0046286 | A1 | 2/2008 | Halsted |
| 2008/0072439 | A1 | 3/2008 | Steffen et al. |
| 2008/0103834 | A1 | 5/2008 | Reiner |
| 2008/0150699 | A1 | 6/2008 | Ohara et al. |
| 2008/0158172 | A1 | 7/2008 | Hotelling et al. |
| 2008/0224917 | A1 | 9/2008 | Kim et al. |
| 2008/0262714 | A1 | 10/2008 | Abramovich Ettinger |
| 2008/0292192 | A1 | 11/2008 | Seki |
| 2008/0311967 | A1 | 12/2008 | Ronen et al. |
| 2009/0012745 | A1 | 1/2009 | Longman et al. |
| 2009/0135003 | A1 | 5/2009 | Charlier et al. |
| 2009/0138244 | A1 | 5/2009 | Schuler et al. |
| 2009/0254971 | A1 | 10/2009 | Herz et al. |
| 2009/0262078 | A1 | 10/2009 | Pizzi |
| 2009/0272192 | A1 | 11/2009 | Killion et al. |
| 2010/0046766 | A1 | 2/2010 | Gregg et al. |
| 2012/0010836 | A1 | 1/2012 | Shemesh et al. |

OTHER PUBLICATIONS

Cleveland, Robert F. Jr. et al.; "Questions and Answers about Biological Effects and Potential Hazards of Radiofrequency Electromagnetic Fields"; OET Bulletin 56 Fourth Edition; bearing a date of Aug. 1999; 38 pages (including cover pages); Federal Communications Commission, Office of Engineering & Technology.

Classic, Kelly; "Radiofrequency (RF) Radiation"; bearing a date of Dec. 18, 2009; pp. 1-6; located at www.hps.org/hpspublications/articles/rfradiation.html (cached version).

"Consumer Information About Radio Frequency Emissions and Responsible Driving"; Verizon Wireless; bearing a date of 2010; 2 pages; © 2010 Verizon.

"Do cell phones cause behavioral problems?"; bearing a date of Dec. 7, 2010; 1 page; located at http://pagingdrgupta.blogs.cnn.com/2010/12/07/do-cell-phones-cause-behavioral-problems/.

U.S. Appl. No. 12/803,142, Hyde et al.
U.S. Appl. No. 12/925,254, Hyde et al.
U.S. Appl. No. 12/925,938, Hyde et al.
U.S. Appl. No. 12/928,939, Hyde et al.

Greene, Kate; "Hyperlinking Reality via Phones"; Technology Review; bearing a date of Nov. 20, 2006; pp. 1-4; MIT.

Jonietz, Erika; "TR10: Augmented Reality"; Technology Review; bearing a date of Mar. 12, 2007; pp. 1-3; MIT.

Livescience Staff; "Cell Phone Radiation Might Improve Memory"; University of South Florida; bearing a date of Jan. 6, 2010; pp. 1-3.

"Microsoft Demos Augmented Vision"; Technology Review; bearing a date of Mar. 3, 2009; 2 pages; located at http://www.technologyreview.com/computing/22218/?a=f.

Nigam, Anil; "Electromagnetic Radiation (EMR) and Its Effects"; bearing a date of Oct. 18, 2006; pp. 1-4; located at http.ezinearticles.com/?electromagnetic-radiation-(EMR)-and-its-effects.

Osterhout, Jacob E.; "Exposure to radiation from cell phones could help protect against Alzheimer's memory loss: study"; Daily News; bearing a date of Jan. 7, 2010; 1 page.

"Radiology benefit management programs can protect patients from radiation exposure"; bearing a date of Apr. 1, 2010; 1 page; located at http://www.news-medical.net/news/20100401/Radiology-benefit-management-programs-can-protect-patients-from radiation-exposure.aspx.

Scherer, Michael; "Cell-Phone Safety: What the FCC Didn't Test"; Time; bearing a date of Oct. 26, 2010; 3 pages; Time Inc.; located at http://www.time.com/time/printout/0,8816,2027523,00.html.

PCT International Search Report; International App. No. PCT/US2011/001085; Oct. 21, 2011; pp. 1-2.

"10 Tips: Cell Phones & Limiting Radiation Exposure"; bearing a date of Jul. 23, 2008; 2 pages; MMIX, CBS Broadcasting Inc.

"BreezeNET PRO.11 Series Reference Guide"; bearing a date of Jul. 1998; 59 pages; BreezeCOM Ltd.

"Cell Phone & Tower RF Radiation Meter"; Natural Energy Works; printed Sep. 2009; pp. 1-8; Natural Energy Works.

"Cell Phone Radiation Science Review on Cancer Risks and Children's Heatlth"; Environmental Working Group; bearing a date of Sep. 2009; pp. 1-42; Environmental Working Group; located at www.ewg.org/cellphoneradiation/fullreport.

"Choosing a Low Radiation Cell Phone"; PhysOrg.com; bearing a date of Sep. 10, 2009; pp. 1-2; located at http://www.physorg.com/print171788291.html.

"FDA Unveils Initiative to Reduce Unnecessary Radiation Exposure from Medical Imaging"; FDA News Release; bearing a date of Feb. 9, 2010; pp. 1-2; FDA U.S. Food and Drug Administration; located at http://www.fda.gov/NewsEvents/Newsroom/PressAnnouncements/ucm200085.htm.

Grove, Bob; "Zap Checker 270"; MT Review; bearing a date of Jun. 2005; pp. 68-69; Monitoring Times.

Haas, Jane Glenn; "Our Health: Breast cancer linked to cell phones?"; The Orange County Register; bearing a date of Apr. 7, 2010; pp. 1-2; Deseret News Publishing Company; located at http://www.deseretnews.com/article/print/700022713/Our-Health-Bre....

"Microalert 2 Radio/Microwave Alarm"; Natural Energy Works; printed on Sep. 9, 2009; pp. 1-5; located at http://www.orgonelab.org/cart/ymicroalert.htm.

"Radiation Protection from electromagnetic fields emitted by cell phones, computer monitors, and other common sources of EMF"; EMF Safety Products; printed on Jun. 18, 2010; pp. 1-6; Less EMF, Inc.; located at http://www.howweheal.com/emf.htm.

Smith, Chris Silver; "Cell Phone Triangulation Accuracy Is All Over the Map"; bearing a date of Sep. 22, 2008; pp. 1-5; Search Engine Land.

Strock, Jud; "Evaluating Cell-Phone Safety"; EE-Evaluation Engineering; printed on Aug. 6, 2009; pp. 1-5; Nelson Publishing Inc.; located at http://archive.evaluationengineering.com/archive/articles/0501deal.htm.

"Trifield Broadband Electromagnetic Field / Electrosmog Meter"; Natural Energy Works; printed on Sep. 9, 2009; pp. 1-4; located at http://www.orgonelab.org/cart/ytrifield.htm.

"Understanding the Effect of the Human Body on RF Signal Propagation"; Effect of RF on Human Body—An On-Line Tutorial; printed on Nov. 5, 2009; 1 page; located at http://www.connect802.com/human_body_rf.htm.

Walsh, Bryan; "Spotlight a Study on Cell Phones and Cancer"; TIME; bearing a date of May 31, 2010; p. 15.

"ZAP Checker"; bearing a date of 2005; pp. 1-8; Alan Broadband Company.

Zeiler, David; "San Francisco Approves Cellphone Radiation Law"; PC World; bearing a date of Jun. 16, 2010; pp. 1-2.

PCT International Search Report; International App. No. PCT/US 11/01086; Oct. 13, 2011; 2 pages.

* cited by examiner

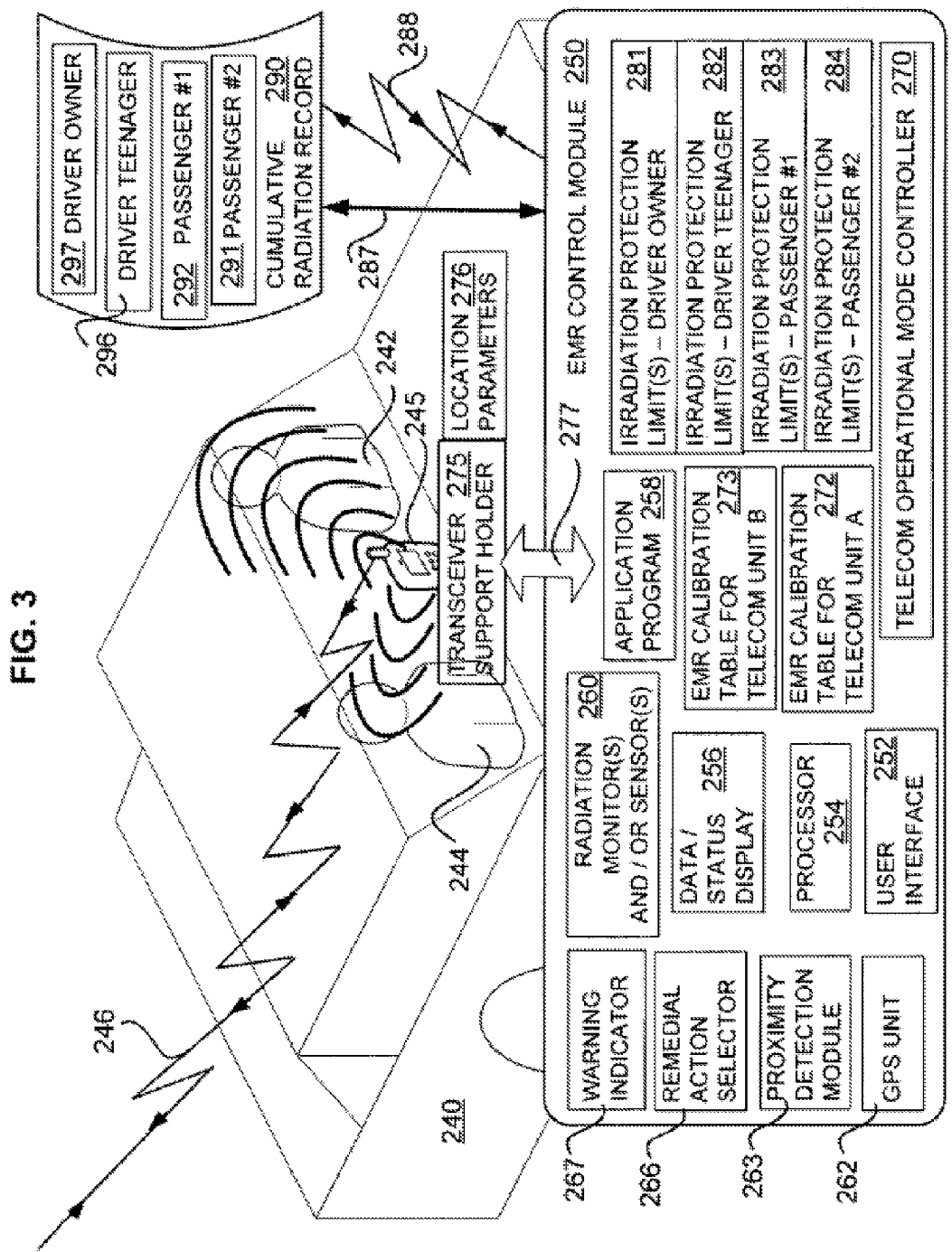

FIG. 4

IRRADIATION EXPOSURE PRIORITY TABLE 365

| User-Related Target Region 370 | User Telecom Device(s) 375 | Real-Time Exposure Threshold Limit 380 | Cumulative Exposure Threshold Limit 385 | Responsive Action 390 |
|---|---|---|---|---|
| Any Body Surface 371 | Mobile Unit CC (fixed location) with Onboard Radiation Sensor 376 | User-Choice SAR 1.6 - 4.0 watts/kg 381 | 386 | Modify Unit Power Mode 391 |
| Heart Appliance 372 (e.g., pacemaker) | Cell Phone DD (variable location) with Offboard Chest Sensor 377 | Per Device Safety Spec 382 | 387 | Turn Off Cell Phone 392 |
| Head, Eyes and/or Ears 373 | Portable Landline phone EE (fixed & variable location) with Proximity Module 378 | SAR 1.6 watts/kg 383 | 388 | Activate Warning Alarm 393 |

RADIATION EMISSION PRIORITY TABLE 310

| 320 Telecom Device Model | 325 User IDs | 330 Operation Mode | 335 Radiation Emissions Range Cap | 340 Actual Radiation Value | 345 User Intrusion Level | 350 Target Region | 355 Real-Time Radiation Limit | 360 Cumulative Radiation Limit |
|---|---|---|---|---|---|---|---|---|
| 323 Mobile BB | 328 Bob Age 65 | Searching 334 | #xx microwatts/cm2 | 344 | 347 | Heart/Lungs | 358 | 363 |
|  |  | Transmit/Receive | #yy microwatts/cm2 | 343 |  | Hearing Aid | 357 | 362 |
| 321 Cell Phone AA | 326 Amy Pregnant | Searching 331 | #qq microwatts/cm2 | 342 337 | 346 | Torso & Reproductive Organs 351 | 353 356 | 361 |
|  |  | Transmit/Receive | #zz microwatts/cm2 | 341 |  |  |  |  |

DATA TABLES FOR VARIED EMISSION & EXPOSURE VALUES

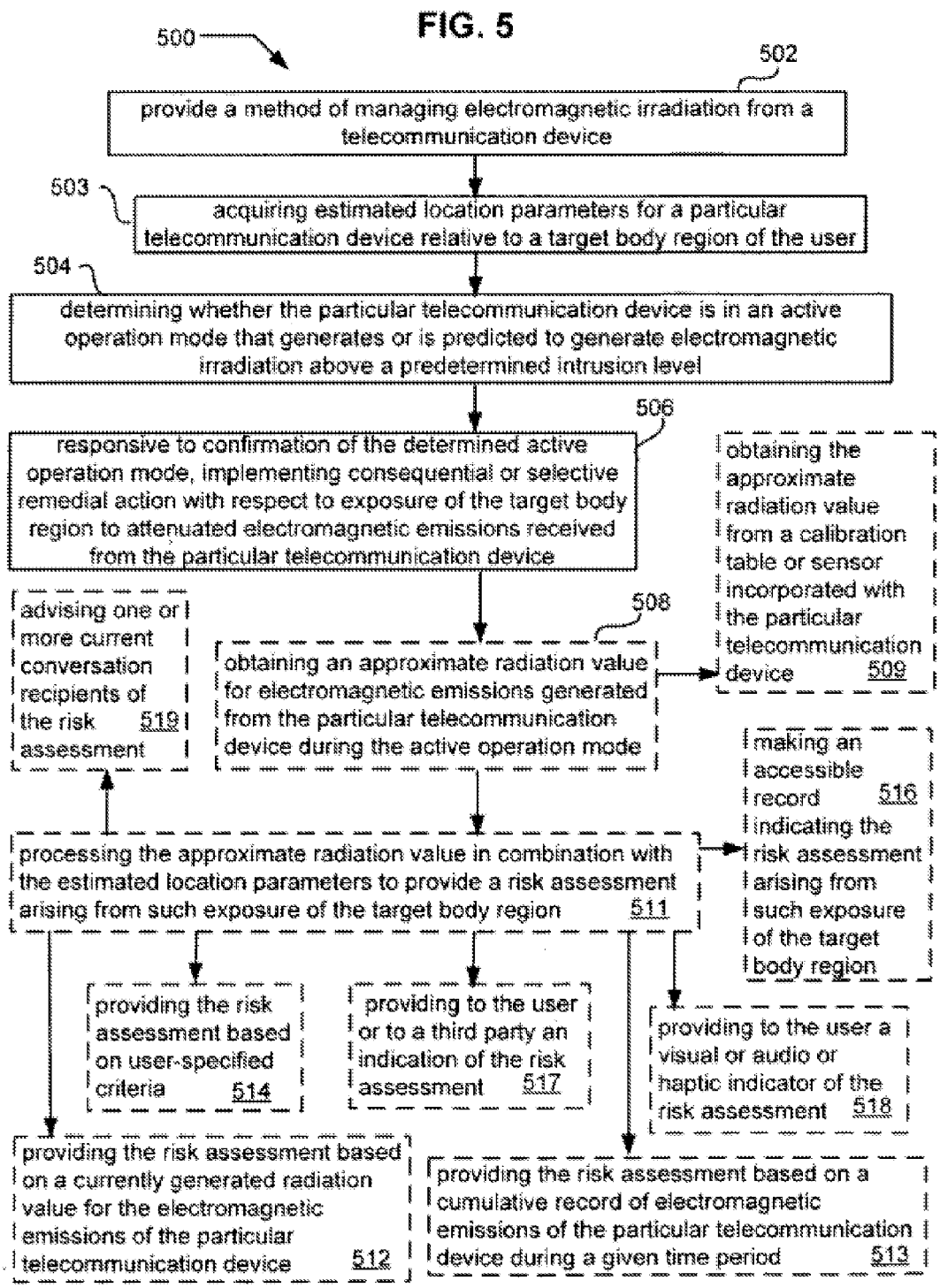

FIG. 17

830 → identifying the specified target body region of a user that is proximate to a particular communication device capable of generating electromagnetic emissions that subject the specified target body region to irradiation exposure  802

↓ establishing whether such irradiation exposure does exceed or is predicted to exceed a safety threshold correlated with the specified target body region  804

→ implementing automatic or programmed remedial action to reduce the irradiation exposure to a dosage value at or below the safety threshold  834  803

↓ if such irradiation exposure has a dosage value above the safety threshold, providing a responsive output based on a possible risk relative to such irradiation exposure

↓ transmitting the responsive output to a local or remote control module, wherein the responsive output includes a recognizable output signal indicative of a current and / or cumulative dosage value that exceeds the safety threshold  832

↓ implementing automatic or programmed remedial action to minimize exposure of the specified target body portion to excessive irradiation  833

→ identifying one or more of the following types of specified target body-related regions: head, eye, ear, heart, chest, stomach, torso, abdomen, groin, reproductive organ, proximate body surface, vulnerable organ, sensitive body part, cerebral portion, cardio-vascular portion, bionic repair, bionic replacement, implanted medical appliance, therapeutic device, health monitoring apparatus, testing unit, diagnostic component, body accessory  839

→ causing the particular communication device to implement one or more of the following: reduced power mode, dormant operation mode, intermittent active mode, temporary alternate mode, power off mode, conversation time limit, different cell tower, optional network carrier, alternate relay/retransmitter, new satellite link, different transmission destination  836

→ causing the particular communication device to change one or more of the following operation parameters to achieve a reduced level of irradiation exposure: frequency, polarity, voltage, current, intensity, orientation, emission mode, transmission pattern, pulse format, control channel, voice channel, audio volume, voice sensitivity  837

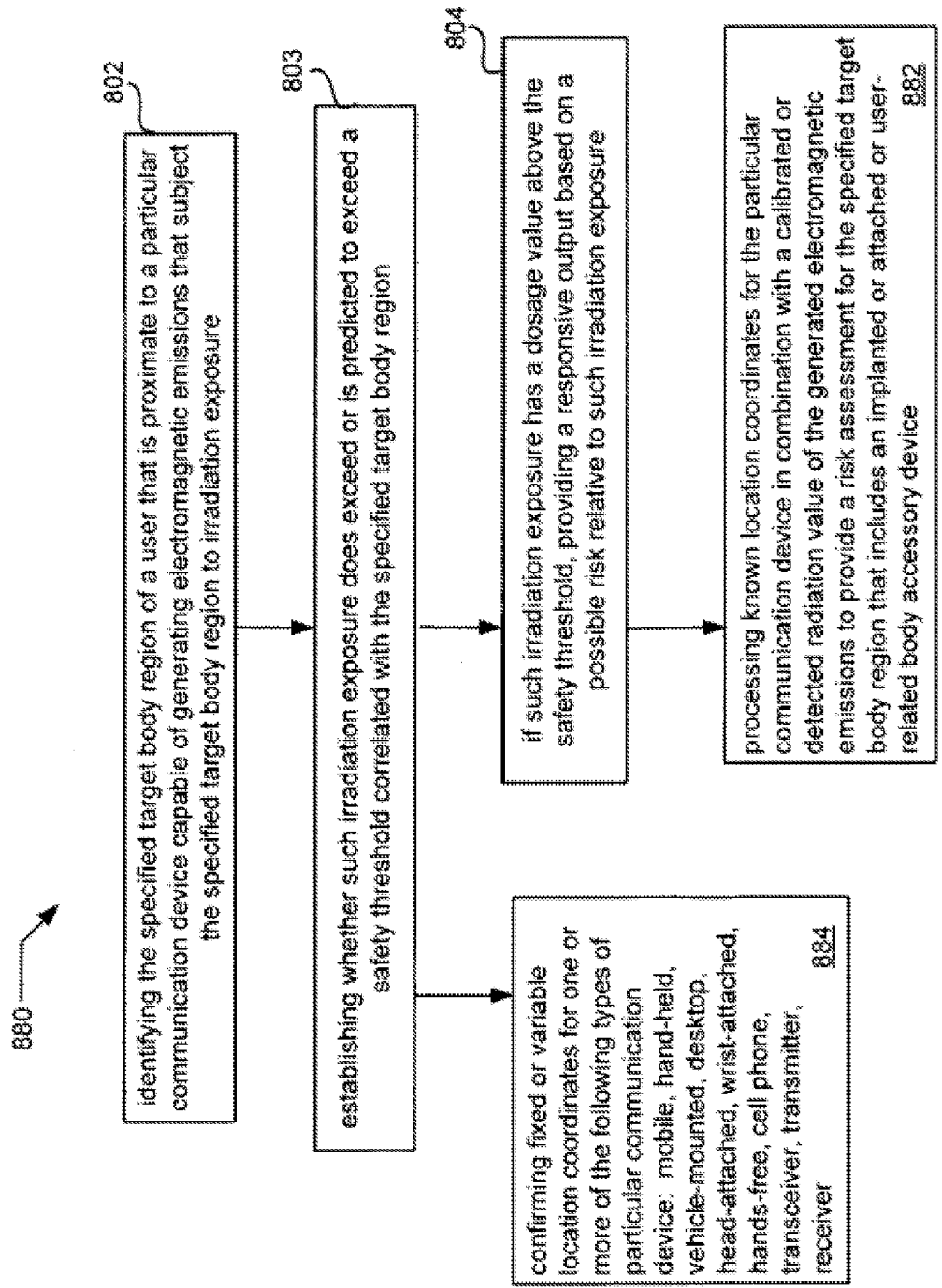

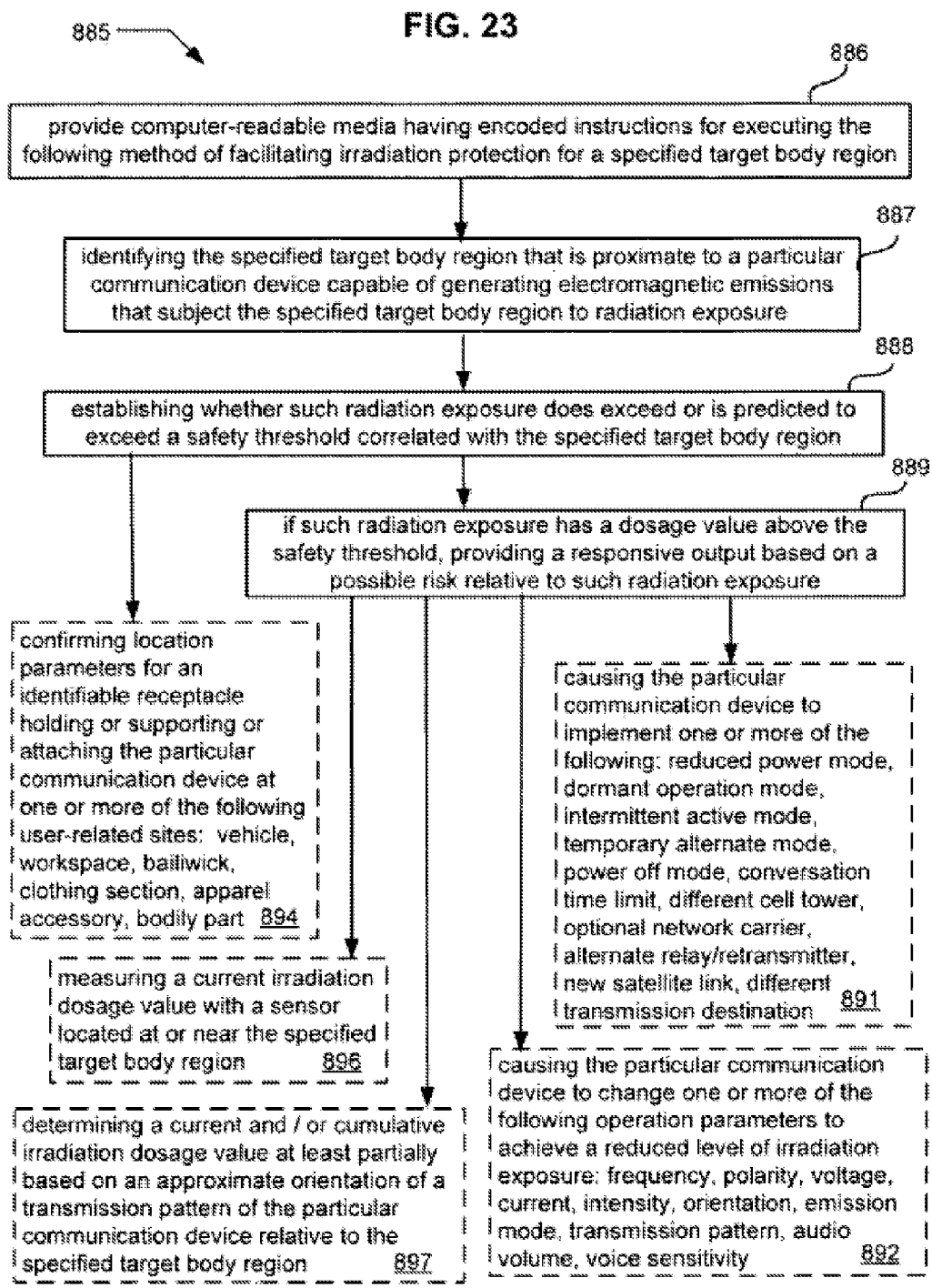

IRRADIATION SELF-PROTECTION FROM USER TELECOMMUNICATION DEVICE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 12/803,142 entitled PERSONAL TELECOMMUNICATION DEVICE WITH TARGET-BASED EXPOSURE CONTROL, naming Roderick A. Hyde, Muriel Y. Ishikawa, Jordin T. Kare, Thomas J. Nugent, Jr., Clarence T. Tegreene, Thomas A. Weaver, Lowell L. Wood, Jr., Victoria Y. H. Wood as inventors, filed on Jun. 18, 2010, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent application(s) as set forth above, but expressly points out that such designations are not to be construed in any way as any type of commentary and/or admission as to whether or not the present application contains any new matter in addition to the matter of its parent application(s).

BACKGROUND

The present application relates to electromagnetic radiation monitoring and control devices and related methods, systems, components, computerized apparatus, software program products, and communication techniques.

SUMMARY

In one aspect, an exemplary method for managing electromagnetic irradiation from a telecommunication device may include acquiring estimated location parameters for a particular telecommunication device relative to a target body region of a user; determining whether the particular telecommunication device is in an active operation mode that generates or is predicted to generate electromagnetic irradiation above a predetermined intrusion level; and responsive to confirmation of the determined active operation mode, implementing consequential or selective remedial action with respect to exposure of the target body region to attenuated electromagnetic emissions received from the particular telecommunication device.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In another aspect, an exemplary system includes but is not limited to computerized components for managing electromagnetic irradiation from a telecommunication device, which system has the capability to implement the various process features disclosed herein. Various exemplary system aspects are described in the claims, drawings, and text forming a part of the present disclosure.

Some system embodiments for managing electromagnetic irradiation from a telecommunication device may include means for acquiring estimated location parameters for a particular telecommunication device relative to a target body region of a user; means for determining whether the particular telecommunication device is in an active operation mode that generates or is predicted to generate electromagnetic irradiation above a predetermined intrusion level; and means configured to be responsive to confirmation of the determined active operation mode in order to implement consequential or selective remedial action with respect to exposure of the target body region to attenuated electromagnetic emissions received from the particular telecommunication device.

Other system embodiments for managing electromagnetic irradiation from a telecommunication device may include proximity determination means for acquiring estimated location parameters for a particular telecommunication device relative to a target body region of a user; monitoring means for determining whether the particular telecommunication device is in an active operation mode that generates or is predicted to generate electromagnetic irradiation above a predetermined intrusion level; and control module means configured to be responsive to confirmation of the determined active operation mode in order to implement consequential or selective remedial action with respect to exposure of the target body region to attenuated electromagnetic emissions received from the particular telecommunication device.

In a further aspect, a computer program product may include computer-readable media having encoded instructions for executing an exemplary method for managing electromagnetic irradiation, wherein the exemplary method may include acquiring estimated location parameters for a particular telecommunication device relative to a target body region of a user; determining whether the particular telecommunication device is in an active operation mode that generates or is predicted to generate electromagnetic irradiation above a predetermined intrusion level; and responsive to confirmation of the determined active operation mode, implementing remedial action to minimize the electromagnetic irradiation of the target body region.

In addition to the foregoing, various other method and/or system and/or program product aspects are set forth and described in the teachings such as text (e.g., claims and/or detailed description) and/or drawings of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 3 is a schematic block diagram depicting exemplary irradiation protection aspects regarding telecommunication units associated with a vehicle.

FIG. 4 shows exemplary data tables for varied emission and exposure values.

FIG. 5 is a high level flow chart for exemplary irradiation protection features.

FIGS. 16-22 are detailed flow charts illustrating further exemplary process aspects regarding irradiation protection.

FIG. 23 is a diagrammatic flow chart for other exemplary computer readable media embodiment features.

DETAILED DESCRIPTION

Figure 1:
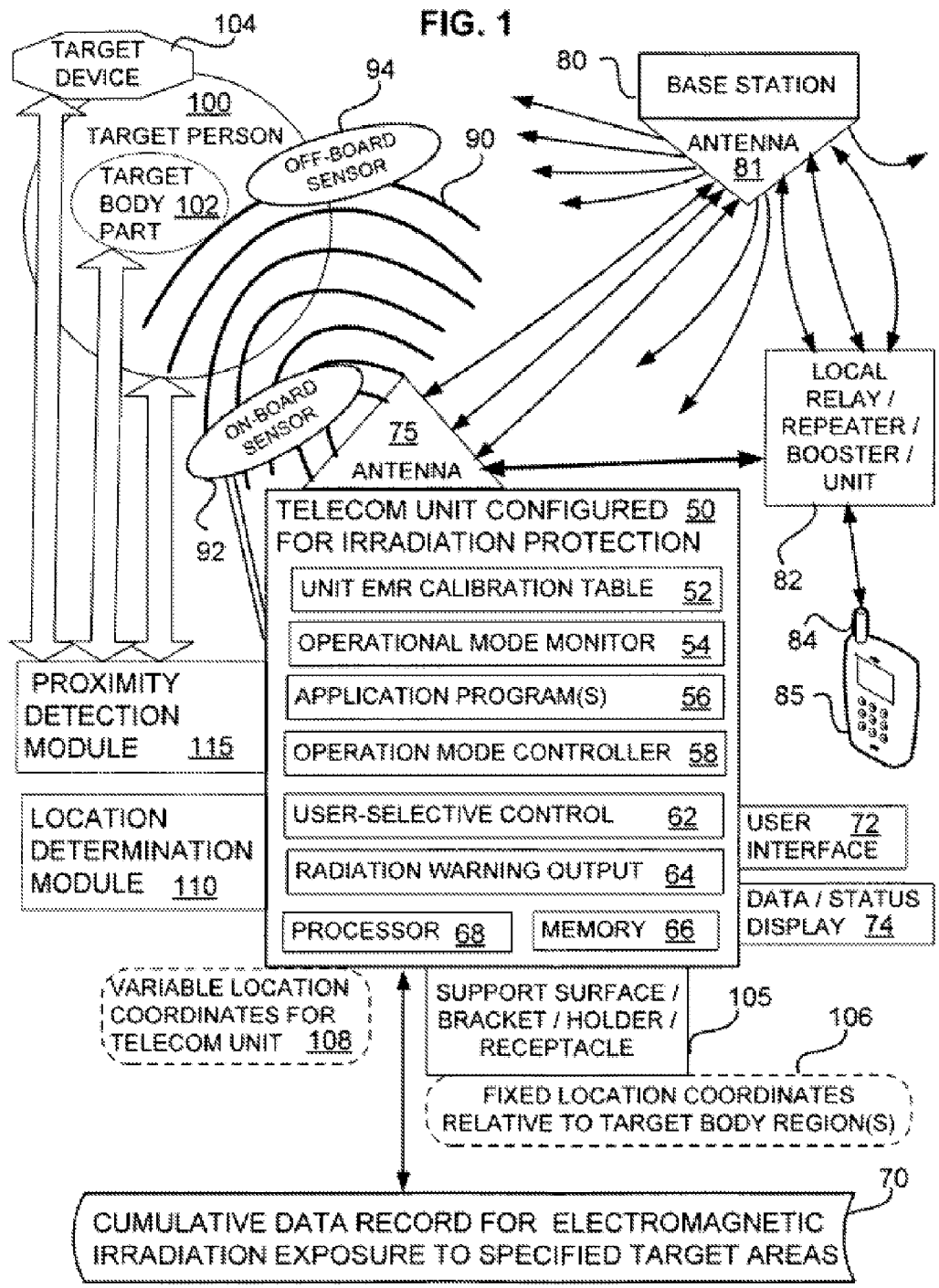
FIG. 1 is a schematic block diagram illustrating exemplary embodiment features for a telecommunication unit configured to provide irradiation protection.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences.

In other implementations, source or other code implementation, using commercially available and/or techniques in the art, may be compiled/implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

Those skilled in the art will recognize that it is common within the art to implement devices and/or processes and/or systems, and thereafter use engineering and/or other practices to integrate such implemented devices and/or processes and/or or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory or location even if components are located outside the territory or location. For example, in a distributed computing context, use of a distributed computing system may occur in a territory or location even though parts of the system may be located outside of the territory or location (e.g., relay, server, processor, signal-bearing medium, transmitting computer, receiving computer, etc. located outside the territory or location).

A sale of a system or method may likewise occur in a territory even if components of the system or method are located and/or used outside the territory. Further, implementation of at least part of a system for performing a method in one territory does not preclude use of the system in another territory.

As used herein, the term "vehicle" encompasses devices for conveying persons or objects, including without limitation automobiles, trucks, motorcycles, buses, trains, and other land conveyances, boats, ferries, ships, and other watergoing vessels, and aircraft.

FIG. 1 is a schematic block diagram illustrating exemplary embodiment features for an irradiation protection system regarding attenuated electromagnetic radiation emissions 90 generated from a telecommunication unit 50 toward a target person 100, a target body part 102, and/or a target device 104 associated with the target person 100. One or more user telecommunication units 50, 85 may respectively include antennas 75, 84 for data transmissions directly to or from antenna 81 of base station 80. In some instances such data transmissions may be facilitated indirectly via a local relay or repeater or booster unit 82.

The illustrated embodiment for telecommunication (telecom) unit 50 is configured to include various components that facilitate irradiation protection, include an electromagnetic radiation (EMR) calibration table 52, operation mode monitor 54, one or more application programs 56, operation mode controller 58, user-selective control 62, radiation warning output 64, memory 66 and processor 68. Additional features may include user interface 72 and data/status display 74.

Some system embodiments may provide a receptacle 105 (e.g., surface, bracket, holder, etc.) adapted to position the telecommunication unit 50 for functional availability to a user. It will be understood that an evaluation of irradiation risks regarding the target person 100 or target body part 102 or target device 104 may be at least partially dependent on determining an approximate location for the telecommunication unit 50 during an active operation mode. Accordingly a system feature may include a location determination module 110 for obtaining fixed telecom unit location coordinates relative to one or more target body regions 106, as well as obtaining variable telecom location coordinates relative to one or more target body regions 106. The location determination module may be incorporated with or otherwise linked with the telecom unit 50 for appropriate data processing regarding irradiation risks.

It will be understood that in some circumstances the telecom location coordinates may already be known or predetermined (e.g., mounted in an identifiable given location relative to a user's body). However in other circumstances variable telecom location coordinates may be obtained in real time (e.g., a hand-held mobile telecom unit) in order to evaluate an irradiation exposure risk for a target body region of a user.

It will be further understood that an evaluation of irradiation risks may be at least partially dependent on determining an approximate separation distance between the telecom unit 50 and the target person 100 or target body part 102 or target device 104. Accordingly an exemplary system feature may include a proximity detection module 115 for detecting and/or monitoring such approximate separation distance. In some instances the separation distance may be determined relative to the antenna 75 (e.g., internal or external antenna) of the telecom unit 50, or relative to the receptacle 105 for the telecom unit 50, or relative to another identifiable aspect of the telecom unit 50.

Additional possible system components for detection and/or monitoring of electromagnetic emissions generated from the telecom unit 50 may include an on-board sensor 92 incorporated with the telecom unit 50 as well as in some instances an off-board sensor 94 preferably located in close proximity to one or more targeted body regions 100, 102, 104. Such sensors 92, 94 may be desirable for some embodiments to transmit pertinent data via communication links to the telecom unit 50 as well as transmit pertinent data via communication links to a cumulative data record 70 for electromagnetic irradiation exposure to specified target areas. In some embodiments where a calibrated radiation value for the telecom unit 50 has already been determined (e.g., by the manufacturer or seller or user or third party, etc.), the sensors 92, 94 may not be required to provide real-time irradiation data. In other embodiments a previously calibrated radiation value may provide a sufficient basis for suggesting or implementing remedial action that minimizes excessive irradiation exposure of a targeted body region of a user.

Figure 2:
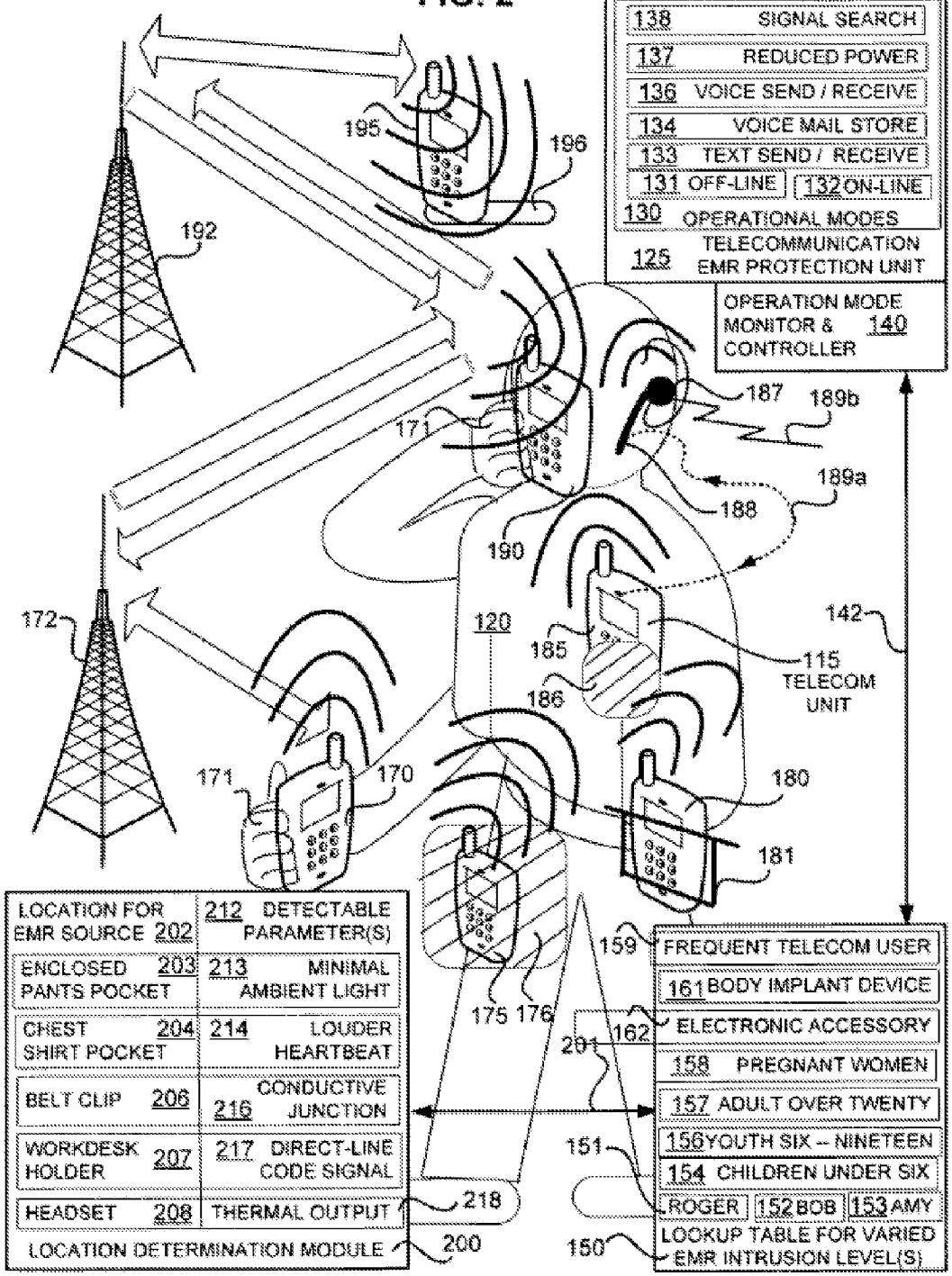
FIG. 2 is a schematic block diagram depicting exemplary irradiation protection aspects regarding telecommunication units at fixed or variable locations relative to a user.

FIG. 2 is a schematic block diagram depicting exemplary system components configured to provide electromagnetic radiation protection (e.g., risk assessment, output data, warning signal, remedial action, etc.) to a user 120 of a telecom unit 115 (e.g., mobile phone, etc.) that may be operated in various locations relative to the user 120 while sending and/or receiving communication signals directly with another communication transceiver or via a local network or via one or more transmission towers 172, 192. Typical locations for the telecom unit 115 may be handheld 171 (e.g., displaced body location 170, adjacent head location 171) as well as receptacle-type locations in an enclosed pants pocket 175 or partially exposed chest shirt pocket 185 or on a belt 180. Another possible location may be head-mounted with an earpiece 187 and microphone 188 having wired 189a or wireless 189b connections. In some instances the telecom unit 115 may be positioned at a location 195 separate and independent of the user 120 such as on a desk or table 196. Of course other locations are possible, and the depicted locations are for purposes of illustration only.

An exemplary system embodiment for a telecommunication EMR protection unit 125 may include an operation mode monitor & controller 140 configured to monitor and/or control various operational modes 130 of the telecom unit 115 that are related to the generation of radiation emissions. Exemplary operational modes may include off-line 131, on-line 132, text send and/or receive 133, voice mail store 134, voice send and/or receive 136, signal search 137, and reduced power 138. It will be understood that other operational modes could be related to radiation emissions, and the depicted examples are for purposes of illustration only.

The telecommunication EMR protection unit 125 and its operation mode monitor & controller 140 may be operably coupled to a lookup table that includes data for varied EMR intrusion levels 150, wherein one or more such EMR intrusion level may be associated with different target body regions and/or different types of users. As illustrated in FIG. 2, exemplary target body regions may include a body implant device 161, and may further include an electronic body unit 162. Exemplary identifiable individual users of the telecom unit 115 having different irradiation risks as well as in some instance having different selective or consequential remedial actions may include Roger 151, Bob 152 and Amy 153. Exemplary categories of telecom users having different irradiation profiles (e.g. target body region, type of remedial action, cumulative irradiation limits, etc.) may include children under six years of age 154, youngsters in the age range six through nineteen 156, adults over twenty years of age 157, pregnant women 158, and frequent telecom users 159. Depending on the circumstances, some target body regions and some user types may not be applicable, and additional target body regions and other user types may be included in order to customize the irradiation protection.

The telecommunication EMR protection unit 125 and its operation mode monitor & controller 140 may also be operably coupled with a location determination module 200 configured for confirmation of a predetermined and/or real-time location for an EMR source (e.g., mobile telecom unit 115). As illustrated in FIG. 2, such locations may include an enclosed pants pocket 203, chest shirt pocket 204, belt clip 206, workdesk holder 207 and head set 208. The location determination module 200 may be incorporated in the telecom unit 115 or located separately, and is configured to recognize and process a detectable parameter 212 that is associated with and identifies each location.

It will be understood that some system embodiments may include location coordinates for a known location (e.g., receptacle-type location), yet nevertheless require additional confirmation that a mobile version of the telecom unit 115 is currently positioned at such known location. In other system embodiments, a non-mobile version of the telecom unit 115 may always be fixedly attached at such known location (e.g., desktop transceiver, permanent vehicle transceiver, etc.)

For example, detection of minimal ambient light 213 could confirm the real-time location of a mobile version of telecom unit 115 in the enclosed pants pocket 203; detection of a louder heartbeat 214 could confirm the real-time location of a mobile version of the telecom unit 115 in the chest shirt pocket 204, and detection of a conductive junction could confirm the real-time location of a mobile version the telecom unit 115 attached to the belt clip 206.

Other examples may include detection of an activated direct-line code signal 217 as confirmation of the real-time location of the telecom unit 115 in the workdesk holder, and may further include detection of a thermal output 218 as confirmation of the real-time location of the telecom unit 115 as part of the headset 208. Depending on the circumstances, the workdesk holder for some users may constitute a permanent attachment for the telecom unit 115, or may constitute for other users an optional location for a mobile version of the telecom unit 115. Similarly in some circumstances the headset location may be an optional telecom unit location for some users (e.g., only used when driving a vehicle, etc.), or in other circumstances may be a virtually permanent telecom unit location (e.g., telemarketer employee continually making calls while keyboarding results, etc.).

Various technology techniques may be incorporated in the system components depicted in FIG. 2, including circuitry configured to ascertain a separation distance between the EMR source and a targeted body region by processing data obtained by one or more of the following types of proximity measurement and/or location detection techniques: ultrasound, infrared (IR), ultraviolet (UV), radio frequency (RF), radio frequency identification (RFID) tag, capacitive sensor, electromagnetic reflection, phase-change, charge-coupled device (CCD) light detection, thermal sensor, image recognition, and audio time of flight.

An EMR source located in the enclosed pants pocket 203 may provide increased irradiation risk to reproductive organs. An EMR source located in the chest shirt pocket 204 may provide increased irradiation risk to the cardiovascular region (e.g., heart, lungs, heart pacemaker, etc.). An EMR source located on the belt clip 206 may provide increased irradiation risks to the abdomen and to reproductive organs. An EMR source located on a workdesk holder 207 have provide increased cumulative irradiation risk to the entire body. An EMR source located in a headset 208 may provide increased irradiation risk to the cerebral area (e.g. eyes, ears, brain, etc.). It will be understood that in some system embodiments, various types of intrusion levels or warnings or remedial action or the like may be customized to provide appropriate irradiation protection for a particular user of the telecommunication unit 115.

Referring to exemplary features depicted in the schematic block diagram of FIG. 3, a vehicle 240 may have a driver 242 and a passenger 244 who are each potential users of a transceiver 245 capable of sending and or receiving data signals 246 via wireless transmissions. During operational usage, the transceiver 245 may during certain time periods be held in a fixed position by a transceiver support holder 275 having predetermined location parameter 276. The transceiver 245 may have a communication link directly or indirectly with an EMR control module 250 that could be incorporated as part of the transceiver 245 or situated in the vehicle 240 or located remotely from the vehicle 240 depending on the circumstances.

The EMR control module 250 may include a user interface 252, processor 254, data/status display 256, as well as additional components including GPS unit 262, proximity detection module 263, remedial action selector 266, and warning indicator 267 (e.g., visual, aural, musical, etc.). Further possible components may include one or more radiation monitors and/or sensors 260 for detection of radiation emissions generated by the transceiver 245 and/or for monitoring operational modes of transceiver 245 that generate radiation emissions above one or more predetermined intrusion levels. A further component may include a telecom operation mode controller 270 for implementing remedial action such as a modification and/or termination of a currently active operational mode.

Additional reference data features may be provided for different types of transceivers. For example, the EMR control module 250 may include an EMR calibration table for a telecom unit "B" 273 as well as a different EMR calibration table for a telecom unit "A" 272. As a further example, the EMR control module 250 may include radiation profile data for different users, including one or more irradiation protection limits for a driver owner 281, one or more irradiation protection limits for a driver teenager 282, one or more irradiation protection limits for a passenger #1 (see 283), and one or more irradiation protection limits for a passenger #2 (see 284).

Some exemplary embodiments may further provide wired 287 and/or wireless 288 communication links between the EMR control module 250 and a cumulative radiation record 290 for maintaining updated irradiation exposure data applicable to driver owner 297, driver teenager 296, passenger #1 (see 292), and passenger #2 (see 291).

It will be understood that a transceiver 245 that is utilized in variable rather than fixed locations within vehicle 240 may also be subjected to the monitoring and/or control techniques disclosed herein to provide protection to a driver or passenger against excessive irradiation exposure.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

FIG. 4 is a schematic representation of exemplary data tables for varied emission & exposure values. It will be understood that some embodiments may provide emphasis on EMR emission values that are monitored or measured at or in close proximity to a radiation source (e.g., a user's telecom unit). Other embodiments may provide emphasis on irradiation dosage values that are monitored or measured at or in close proximity to a body-related target region (e.g., head, medical appliance, reproductive organs, etc.) Other embodiments may provide current or cumulative irradiation protection information and/or remedial action based on processing EMR radiation and dosage values obtained from diverse sensors and/or monitors and/or data records.

A radiation emission priority table 310 may include data for multiple user IDs 325 associated with one or more particular telecommunication device models 320. For purposes of illustration, reference is made to a commonly used power density measurement unit for characterizing an electromagnetic field. As used herein, power density measurements per unit area are expressed in terms of microwatts per square centimeter. Such measurements may provide reasonable accuracy when the point of measurement is a sufficient distance away from EMR emitter (e.g., more than several wavelengths distance from a typical EMR source).

As a first example, a cell phone "AA" (see 321) for a user identified as "Amy pregnant" (see 326) may include a searching 331 operation mode having a pre-calibrated radiation emissions range cap 335 with a value or "#qq microwatts/square cm" (see 337). Amy may have a user intrusion level 345 that applies to her individually (see 346). In addition, actual radiation values 340 for Amy may be obtained by detection or monitoring (see 342) during the searching 331. With respect to a target region 350 for Amy that includes her torso & reproductive organs (see 351), a correlated real-time radiation limit 355 may be selected or automatically determined (see 356), and a correlated cumulative radiation limit 360 may be selected or automatically determined (see 361).

As another example for Amy, a transmit/receive 332 operation mode may have a pre-calibrated radiation emissions range cap 335 with a value or "#zz microwatts/square cm" (see 338). In addition, actual radiation values 340 for Amy may be obtained by detection or monitoring (see 343) during the transmit/receive 333. With respect to a same target region 350 for Amy that includes her torso & reproductive organs (see 351), a same correlated real-time radiation limit 355 may be selected or automatically determined (see 356), and a same correlated cumulative radiation limit 360 may be selected or automatically determined (see 361).

As a second example, a mobile unit "BB" (see 323) for a user identified as "Bob age 65" (see 328) may include a searching 334 operation mode having a pre-calibrated radiation emissions range cap 335 with a value or "#xx microwatts/square cm" (see 339). Bob may have a user intrusion level 345 that applies to him individually (see 347). In addition, actual radiation values 340 for Bob may be obtained by detection or monitoring (see 344) during the searching mode 334. With respect to a target region 350 for Bob that includes his heart/lungs (see 354), a correlated real-time radiation limit 355 may be selected or automatically determined (see 358), and a correlated cumulative radiation limit 360 may be selected or automatically determined (see 363).

As another example for Bob, a transmit/receive 333 operation mode may have a pre-calibrated radiation emissions range cap 335 with a value or "#yy microwatts/square cm" (see 338). In addition, actual radiation values 340 for Bob may be obtained by detection or monitoring (see 343) during the transmit/receive mode 333. With respect to a target region 350 for Bob that includes his hearing aid (see 353), a correlated real-time radiation limit 355 may be selected or automatically determined (see 357), and a correlated cumulative radiation limit 360 may be selected or automatically determined (see 362).

Further exemplary system embodiments shown in FIG. 4 include an irradiation exposure priority table 365 for various user-related target regions 370 associated with one or more particular telecommunication devices 375. For purposes of illustration, reference is made to an irradiation exposure standard adopted by the FCC (Federal Communications Commission), which standard is based on a specific absorption rate (SAR) measured by the amount of a telecom unit's radiation energy in watts absorbed per kilogram of tissue.

As a first example, an applicable user-related target region 370 may includes any body surface (see 371) of the user. An applicable user telecom device 375 may include a fixed location mobile unit "CC" with an onboard radiation sensor (see 376) having a real-time exposure threshold limit 380 based on user-choice in a range of SAR 1.6-4.0 watts per kilogram (see 381). A related cumulative exposure threshold limit 385 that is selected or otherwise determined may have a particular dosage exposure value (see 386). In a situation wherein one or the other of the predetermined threshold limits 381, 386 is exceeded, an appropriate responsive action 390 may cause a selective or consequential remedial action such as "modify telecom unit power mode" (see 391).

As another example, an applicable user-related target region 370 may include a heart appliance such as a pacemaker (see 372) of the user. An applicable user telecom device 375 may include a variable location cell phone "DD" with an onboard chest sensor (see 377) having a real-time exposure threshold limit 380 based on the heart appliance device safety specification (see 382). A related cumulative exposure threshold limit 385 that is selected or otherwise determined may have a particular dosage exposure value (see 387). In a situation wherein one or the other of the predetermined threshold limits 381, 386 is exceeded, an appropriate responsive action 390 may cause a selective or consequential remedial action such as "turn off cell phone" (see 392).

As an additional example, an applicable user-related target region 370 may include the head, eyes and/or ears (see 373) of the user. An applicable user telecom device 375 may include a fixed and variable location portable landline phone "EE" (see 378) having a real-time exposure threshold limit 380 that is selected or otherwise determined to be SAR 1.6 watts per kilogram (see 383). A related cumulative exposure threshold limit 385 that is selected or otherwise determined may have a particular dosage exposure value (see 388). In a situation wherein one or the other of the predetermined threshold limits 383, 388 is exceeded, an appropriate responsive action 390 may cause a selective or consequential remedial action such as "activate warning alarm" (see 393).

It will be understood that the specific types of radiation protection information depicted in the exemplary data tables of FIG. 4 are for purposes of illustration and are not intended to be limiting. Additional categories and applicable data values and remedial actions may be provided in accordance with a user's preference or to a third party's decision or a product manufacturer's specification or other entity which may be responsible for administering the various irradiation protection schemes disclosed herein.

It will be understood that the exemplary system embodiments disclosed herein facilitate managing electromagnetic irradiation from a telecommunication device, and may include proximity determination means (e.g., proximity detection modules 115, 263, proximity detection device 695) for acquiring estimated location parameters for a particular telecommunication device relative to a target body region of a user, as well as monitoring means (e.g., operational mode monitors 54, 140) for determining whether the particular telecommunication device is in an active operation mode that generates or is predicted to generate electromagnetic irradiation above a predetermined intrusion level. Additional system components may include control module means (e.g., operation mode controllers 58, 140, 270) configured to be responsive to confirmation of the determined active operation mode in order to implement consequential or selective remedial action (e.g., lookup table 700) with respect to exposure of the target body region to attenuated electromagnetic emissions received from the particular telecommunication device.

It will be further understood that the exemplary system embodiments disclosed herein may include means for acquiring estimated location parameters (e.g., location determination modules 110, 200) for a particular telecommunication device relative to a target body region of a user. Further exemplary system components may include means for determining whether the particular telecommunication device is in an active operation mode (e.g., operation mode monitor & controller 140, application program 258) that generates or is predicted to generate electromagnetic irradiation above a predetermined intrusion level (e.g., lookup table 150, irradiation protection limits 281, 282, 283, 284). Additional exemplary system components may include means (e.g., telecom unit 50, control module 250) configured to be responsive to confirmation of the determined active operation mode in order to implement consequential or selective remedial action (e.g., responsive action 390) with respect to exposure of the target body region to attenuated electromagnetic emissions received from the particular telecommunication device.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

Referring to the high level flow chart of FIG. 5, an exemplary process embodiment 500 provides a method of managing electromagnetic irradiation from a telecommunication device (block 502) that may include acquiring estimated location parameters for a particular telecommunication device relative to a target body region of a user (block 503), determining whether the particular telecommunication device is in an active operation mode that generates or is predicted to generate electromagnetic irradiation above a predetermined intrusion level (block 504); and responsive to confirmation of the determined active operation mode, implementing consequential or selective remedial action with respect to exposure of the target body region to attenuated electromagnetic emissions received from the particular telecommunication device (block 506).

Other possible process components may include obtaining an approximate radiation value for electromagnetic emissions generated from the particular telecommunication device during the active operation mode (block 508), and obtaining the approximate radiation value from a calibration table or sensor incorporated with the particular telecommunication device (block 509). Additional process aspects may include processing the approximate radiation value in combination with the estimated location parameters to provide a risk assessment arising from such exposure of the target body region (block 511). Further related risk assessment aspects may include providing the risk assessment based on a currently generated radiation value for the electromagnetic emissions of the particular telecommunication device (block 512), providing the risk assessment based on a cumulative record of electromagnetic emissions of the particular telecommunication device during a given time period (block 513), and providing the risk assessment based on user-specified criteria (block 541).

Other risk assessment features may include making an accessible data record indicating the risk assessment arising from such exposure of the target body region (block 516), providing to the user or to a third party an indication of the risk assessment (block 517), and providing to the user a visual or audio or haptic indicator of the risk assessment (block 518). Another possible risk assessment feature may include advising one or more current conversation recipients of the risk assessment (block 519).

Figure 6:
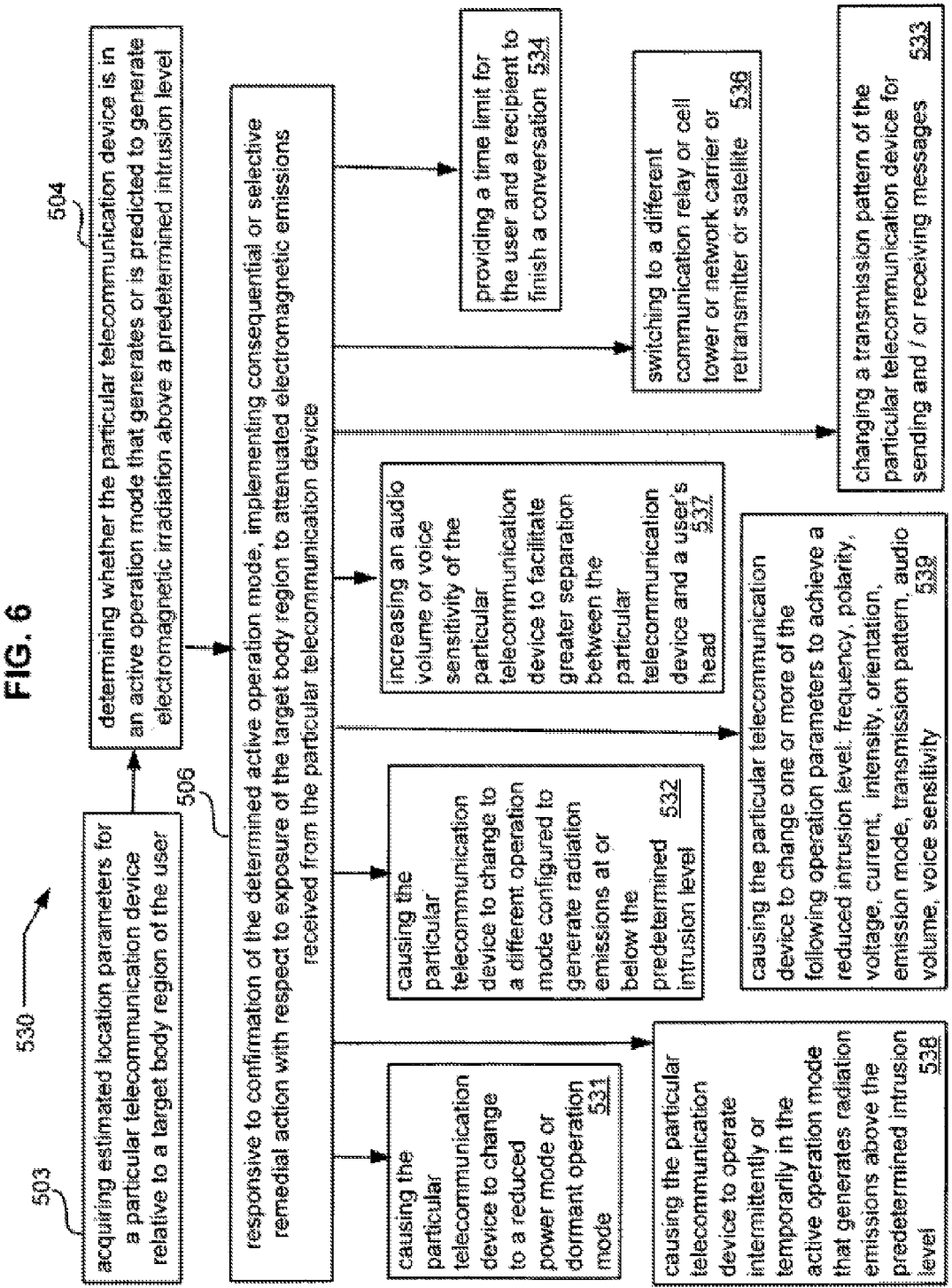
FIGS. 6-12 are more detailed flow charts illustrating further exemplary process features that may be incorporated in irradiation protection embodiments.

The process embodiment features 530 illustrated in the detailed flow chart of FIG. 6 may include previously described features 503, 504, 506 along with implementing various types of consequential or selective remedial action regarding irradiation risks. For example, such remedial action may include causing the particular telecommunication device to change to a reduced power mode or dormant operation mode (block 531), and in some instances may include causing the particular telecommunication device to change to a different operation mode configured to generate radiation emissions at or below the predetermined intrusion level (block 532).

Other possible remedial actions may include changing a transmission pattern of the particular telecommunication device for sending and/or receiving messages (block 533), providing a time limit for the user and a recipient to finish a conversation (block 534), and switching to a different communication relay or cell tower or network carrier or retransmitter or satellite (block 536). Some exemplary embodiments may further provide for increasing an audio volume or voice sensitivity of the particular telecommunication device to facilitate greater separation between the particular telecommunication device and a user's head (block 537).

FIG. 6 also depicts additional exemplary types of remedial action such as causing the particular telecommunication device to operate intermittently or temporarily in the active operation mode that generates radiation emissions above the predetermined intrusion level (block 538), as well as causing the particular telecommunication device to change one or more of the following operation parameters to achieve a reduced intrusion level: frequency, polarity, voltage, current, intensity, orientation, emission mode, transmission pattern, audio volume, voice sensitivity (block 539).

Figure 7:
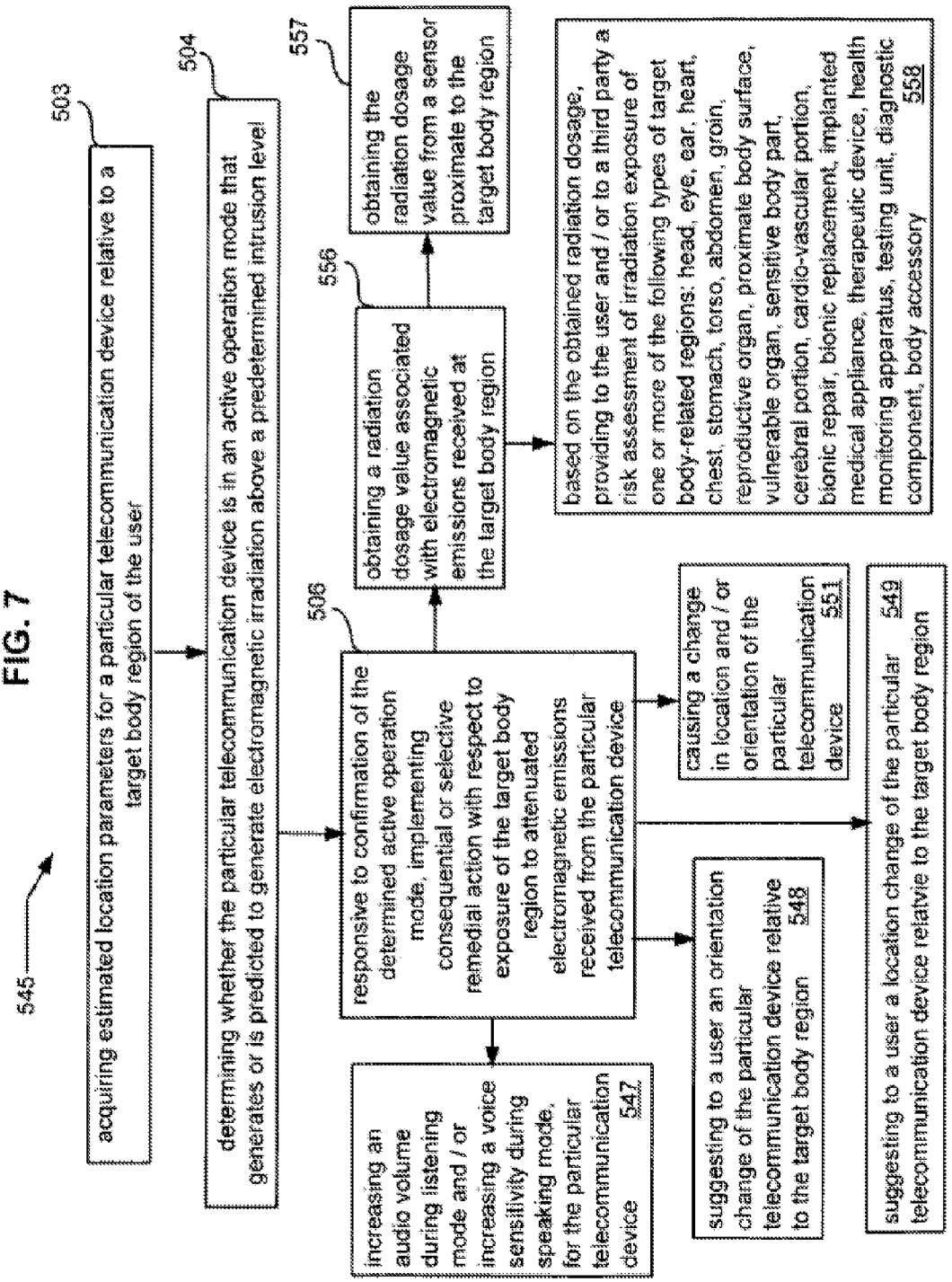

Referring to the various embodiment features 545 illustrated in FIG. 7, a possible process implementation may include previously described operations 503, 504, 506 as well as implementing consequential or selective remedial action such as increasing an audio volume during listening mode and/or increasing a voice sensitivity during speaking mode, for the particular telecommunication device (block 547). Other types of remedial action may include suggesting to a user an orientation change (block 548) or suggesting to a user a location change (block 549) of the particular telecommunication device, relative to the target body region. A further remedial action aspect may include causing a change in location and/or orientation of the particular telecommunication device (block 551).

Some exemplary embodiments may further include obtaining a radiation dosage value associated with electromagnetic emissions received at the target body region (block 556), and obtaining the radiation dosage value from a sensor proximate to the target body region (block 557). Another possible aspect may include based on the obtained radiation dosage, providing to the user and/or to a third party a risk assessment of irradiation exposure of one or more of the following types of target body-related regions: head, eye, ear, heart, chest, stomach, torso, abdomen, groin, reproductive organ, proximate body surface, vulnerable organ, sensitive body part, cerebral portion, cardio-vascular portion, bionic repair, bionic replacement, implanted medical appliance, therapeutic device, health monitoring apparatus, testing unit, diagnostic component, body accessory (block 558).

Figure 8:
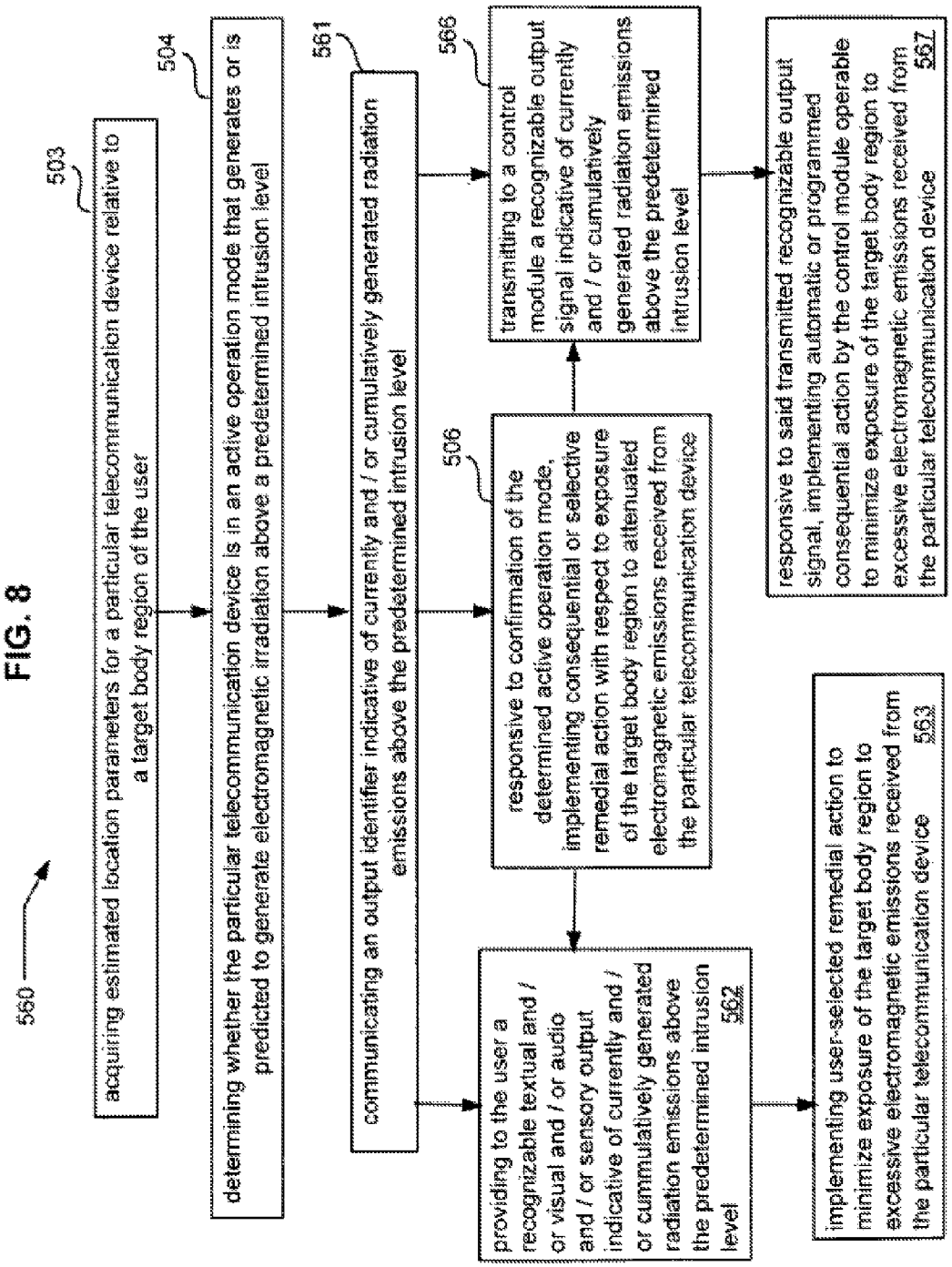

Various exemplary process embodiment features 560 disclosed in the flow chart of FIG. 8 may include previously described components 503, 504, 506 in combination with communicating an output identifier indicative of currently and/or cumulatively generated radiation emissions above the predetermined intrusion level (block 561). A related process aspect may provide to the user the output identifier that includes a recognizable textual and/or visual and/or audio and/or sensory output indicative of currently and/or cumulatively generated radiation emissions above the predetermined intrusion level (block 562). A further related possible aspect may include implementing user-selected remedial action to minimize exposure of the target body region to excessive electromagnetic emissions received from the particular telecommunication device (block 563).

In some instance an exemplary embodiment may include transmitting to a control module a recognizable output signal indicative of currently and/or cumulatively generated radiation emissions above the predetermined intrusion level (block 566), and may further include responsive to said transmitted recognizable output signal, implementing automatic or programmed consequential action by the control module operable to minimize exposure of the target body region to excessive electromagnetic emissions received from the particular telecommunication device (block 567).

Figure 9:
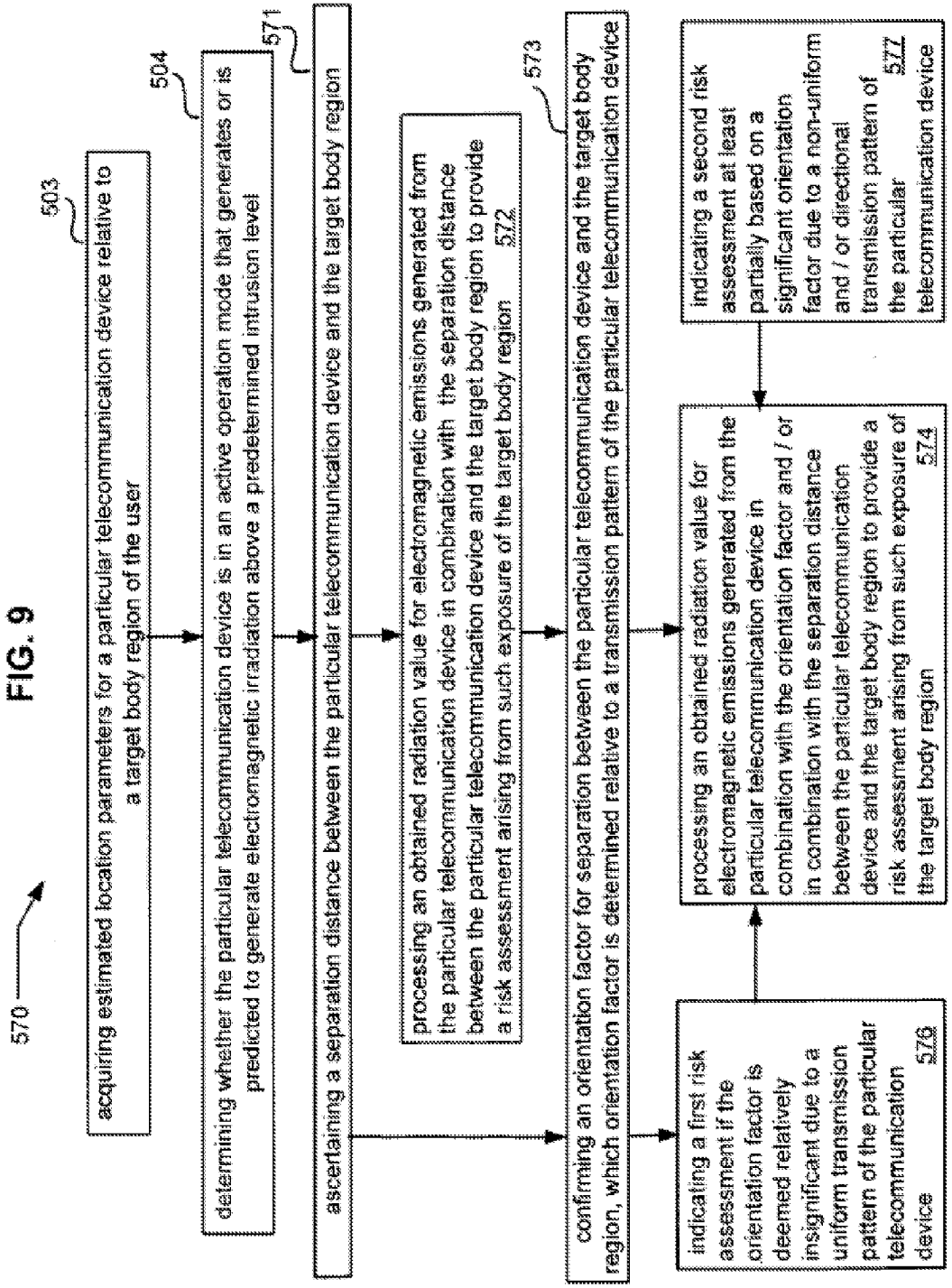

Referring to the detailed flow chart of FIG. 9, exemplary process features 570 may include previously described aspects 503, 504 along with ascertaining a separation distance between the particular telecommunication device and the target body region (block 571). A related aspect may include processing an obtained radiation value for electromagnetic emissions generated from the particular telecommunication device in combination with the separation distance between the particular telecommunication device and the target body region to provide a risk assessment arising from such exposure of the target body region (block 572).

Another possible process feature may include confirming an orientation factor for separation between the particular telecommunication device and the target body region, which orientation factor is determined relative to a transmission pattern of the particular telecommunication device (block 573). A related aspect may include processing an obtained radiation value for electromagnetic emissions generated from the particular telecommunication device in combination with the orientation factor to provide a risk assessment arising from such exposure of the target body region (block 574).

Additional possible risk assessment factors may include indicating a first risk assessment if the orientation factor is deemed relatively insignificant due to a uniform transmission pattern of the particular telecommunication device (block 576), and indicating a second risk assessment at least partially based on a significant orientation factor due to a non-uniform and/or directional transmission pattern of the particular telecommunication device (block 577).

Figure 10:
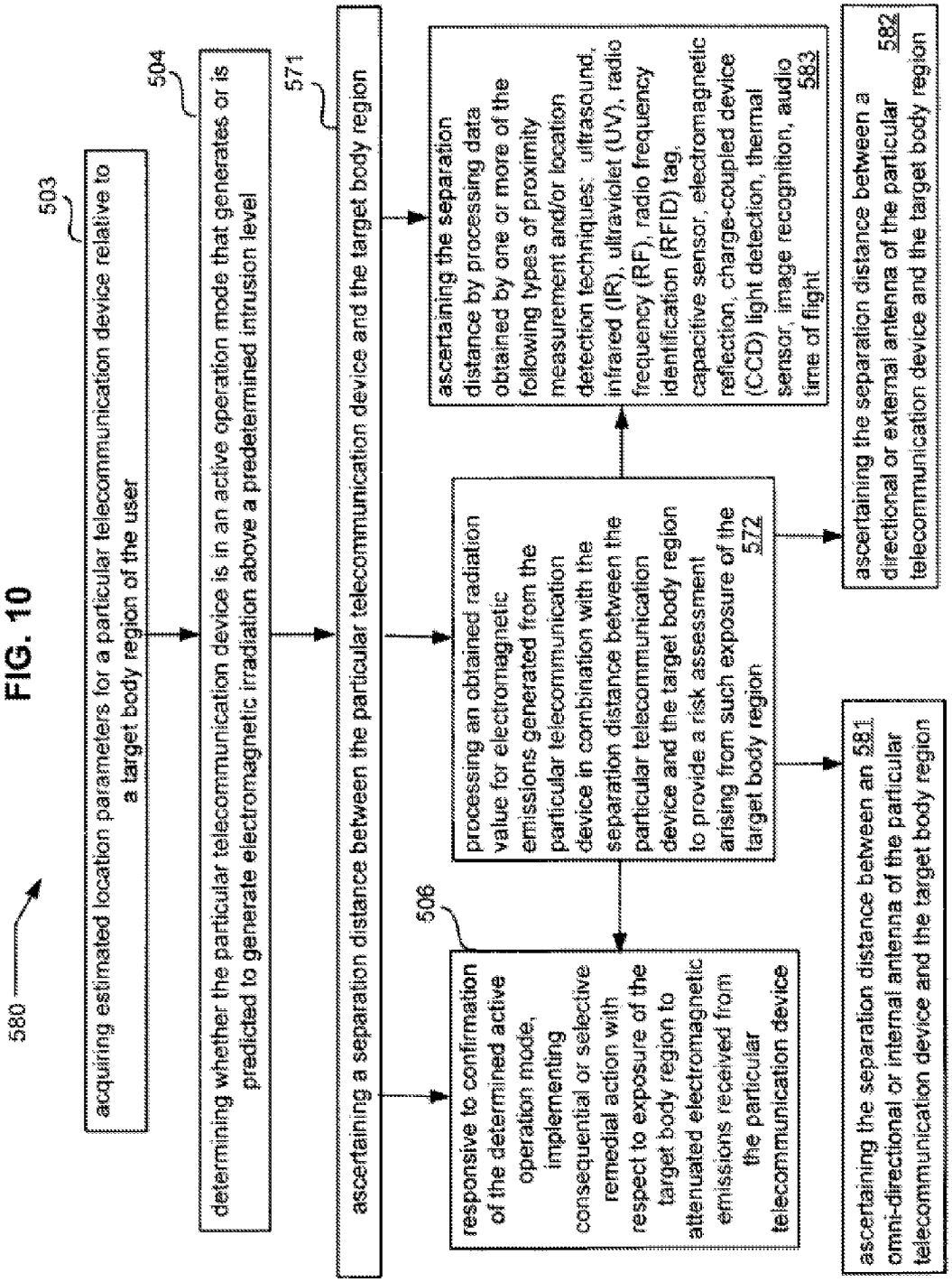

The detailed flow chart of FIG. 10 depicts various exemplary process features 580 including previously described components 503, 504, 506, 571, 572 in combination with various aspects related to the ascertained distance between the particular telecommunication device and the target body region. For example, some possible aspects may include ascertaining the separation distance by one or more of the following types of proximity measurement techniques: ultrasound, infrared (IR), ultraviolet (UV), radio frequency (RF), radio frequency identification (RFID) tag, capacitive sensor, electromagnetic reflection, phase-change, charge-coupled device (CCD) light detection, thermal sensor, image recognition, audio time of flight (block 583).

Additional exemplary embodiments may include ascertaining the separation distance between an omni-directional or internal antenna of the particular telecommunication device and the target body region (block 581). A further possible embodiment feature may include ascertaining the separation distance between a directional or external antenna of the particular telecommunication device and the target body region (block 582).

Figure 11:
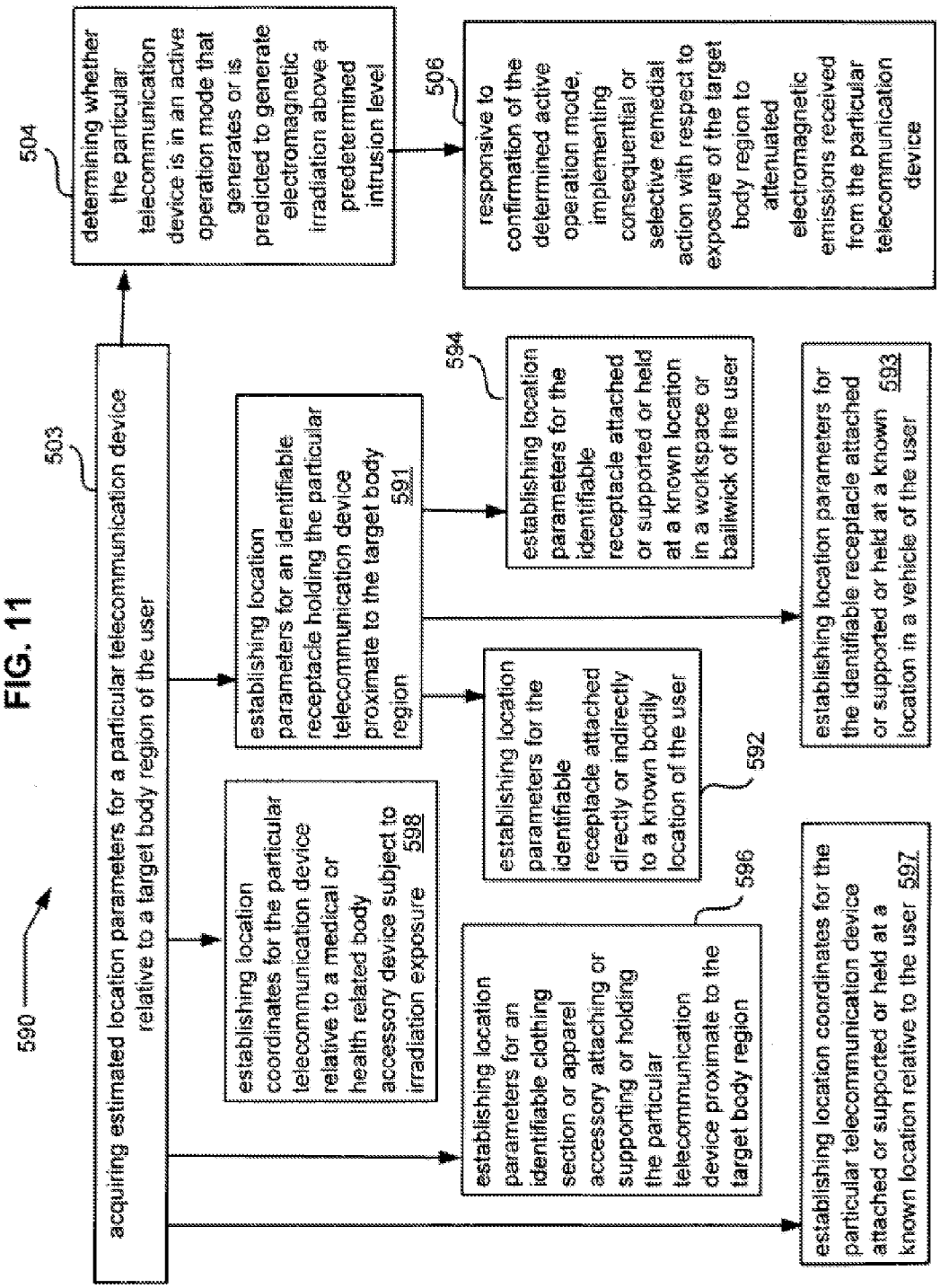

The exemplary process embodiment features 590 of FIG. 11 include previously described operations 503, 504, 506 along with establishing location parameters for an identifiable receptacle holding the particular telecommunication device proximate to the target body region (block 591). Related possible process features may include establishing location parameters for the identifiable receptacle attached directly or indirectly to a known bodily location of the user (block 592), and establishing location parameters for the identifiable receptacle attached or supported or held at a known location in a vehicle of the user (block 593). Additional possible aspects may include establishing location parameters for the identifiable receptacle attached or supported or held at a known location in a workspace or bailiwick of the user (block 594).

Some exemplary embodiment may include establishing location parameters for an identifiable clothing section or apparel accessory attaching or supporting or holding the particular telecommunication device proximate to the target body region (block 596). Other possible features may include establishing location parameters for the particular telecommunication device attached or supported or held at a known location relative to the user (block 597. Further possible enhancements may include establishing location coordinates for the particular telecommunication device relative to a medical or health related body accessory device subject to irradiation exposure (block 598).

Figure 12:
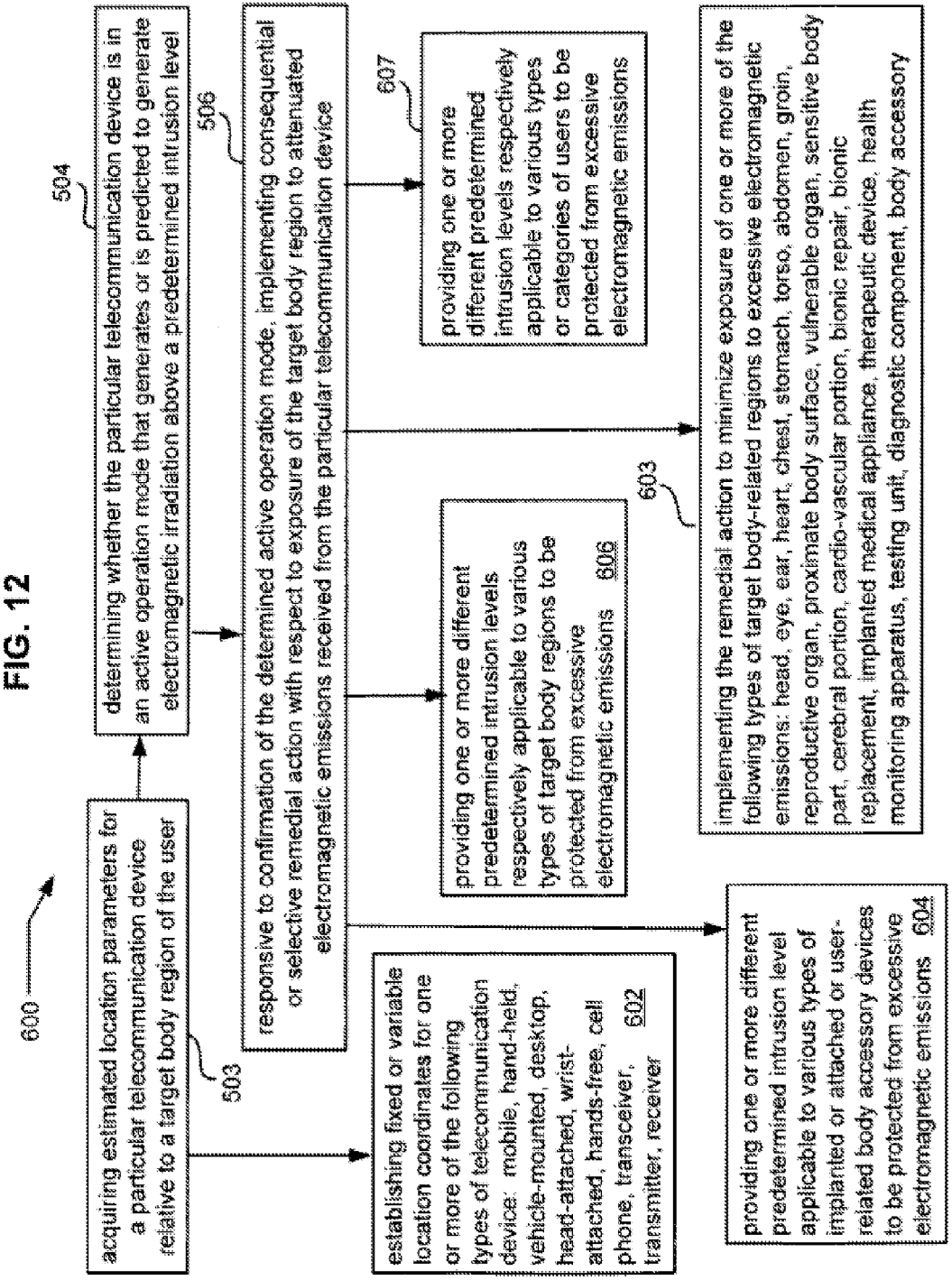

Referring to the detailed flow chart of FIG. 12, variously illustrated embodiment features 600 include previously described process aspects 503, 504, 506 in combination with establishing location parameters for one or more of the following types of telecommunication device: mobile, handheld, vehicle-mounted, desktop, head-attached, wrist-attached, hands-free, cell phone, transceiver, transmitter, receiver (block 602). Other possible process aspects may include implementing the remedial action to minimize exposure of one or more of the following types of target body-related regions to excessive electromagnetic emissions: head, eye, ear, heart, chest, stomach, torso, abdomen, groin, reproductive organ, proximate body surface, vulnerable organ, sensitive body part, cerebral portion, cardio-vascular portion, bionic repair, bionic replacement, implanted medical appliance, therapeutic device, health monitoring apparatus, testing unit, diagnostic component, body accessory (block 603).

Additional possible process features depicted in FIG. 12 may include providing one or more different predetermined intrusion levels respectively applicable to various types of implanted or attached or user-related body accessory devices to be protected from excessive electromagnetic emissions (block 604). Other exemplary embodiment features may include providing one or more different predetermined intrusion levels respectively applicable to various types of target body regions to be protected from excessive electromagnetic emissions (block 606), and providing one or more different predetermined intrusion levels respectively applicable to various types or categories of users to be protected from excessive electromagnetic emissions (block 607).

Figure 13:
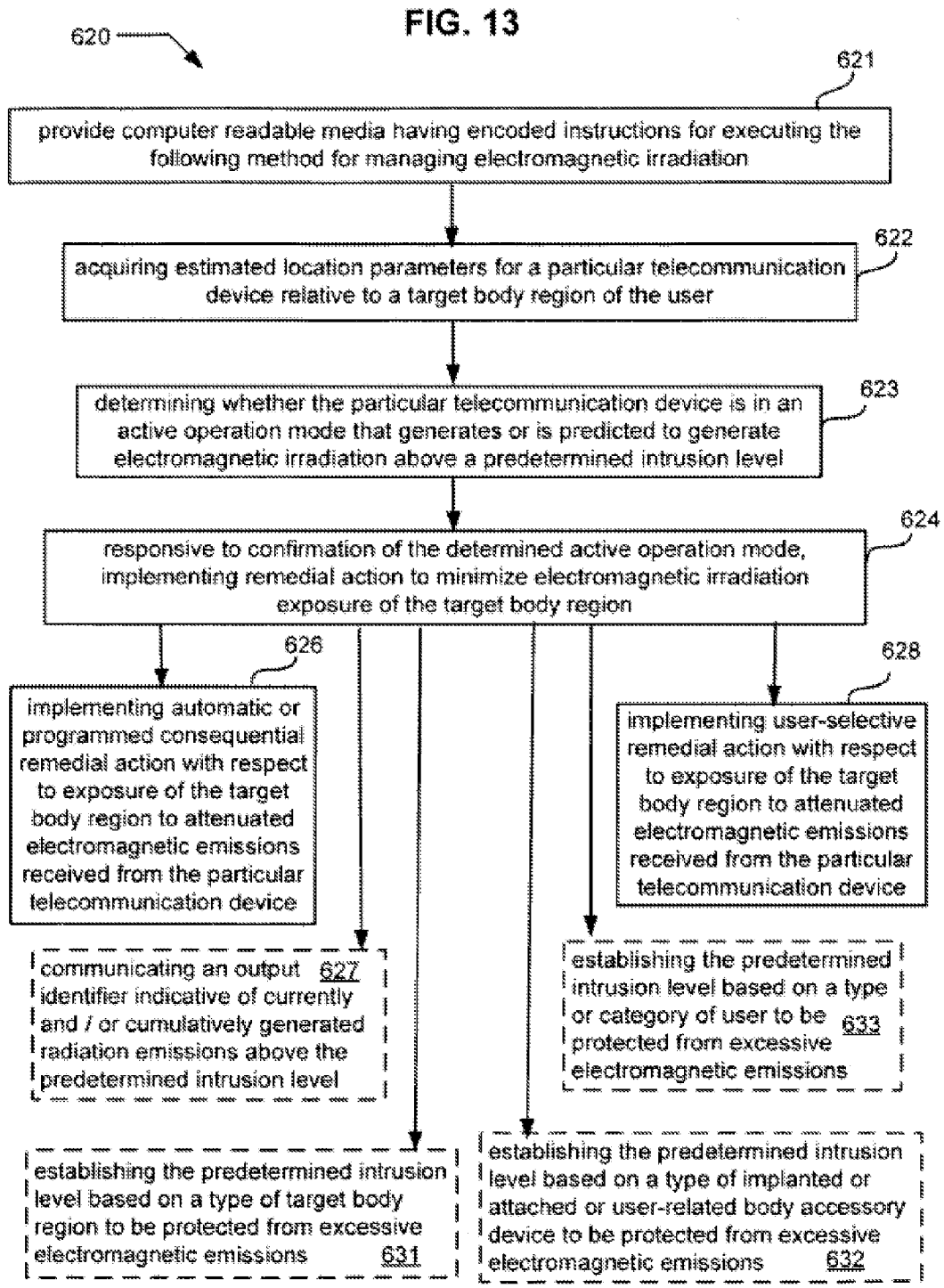
FIG. 13 is a diagrammatic flow chart for exemplary computer readable media embodiment features.

FIG. 13 is a diagrammatic flow chart for an exemplary computer program product 620 that provides computer readable media having encoded instructions for executing a method (block 621), wherein the method may include acquiring estimated location parameters for a particular telecommunication device relative to a target body region of a user (block 622); determining whether the particular telecommunication device is in an active operation mode that generates or is predicted to generate electromagnetic irradiation above a predetermined intrusion level (block 623); and responsive to confirmation of the determined active operation mode, implementing remedial action to minimize the electromagnetic irradiation of the target body region (block 624).

Further possible method features to minimize electromagnetic irradiation may include implementing automatic or programmed consequential remedial action with respect to exposure of the target body region to attenuated electromagnetic emissions received from the particular telecommunication device (block 626), and implementing user-selective remedial action with respect to exposure of the target body region to attenuated electromagnetic emissions received from the particular telecommunication device (block 628).

Other exemplary aspects may include communicating an output identifier indicative of currently and/or cumulatively generated radiation emissions above the predetermined intrusion level (block 627). Further possible process features may include establishing the predetermined intrusion level based on a type of target body region to be protected from excessive electromagnetic emissions (block 631). In some instances an exemplary process feature may include establishing the predetermined intrusion level based on a type of implanted or attached or user-related body accessory device to be protected from excessive electromagnetic emissions (block 632). A further possible aspect may include establishing the predetermined intrusion level based on a type or category of user to be protected from excessive electromagnetic emissions (block 633).

Figure 14:
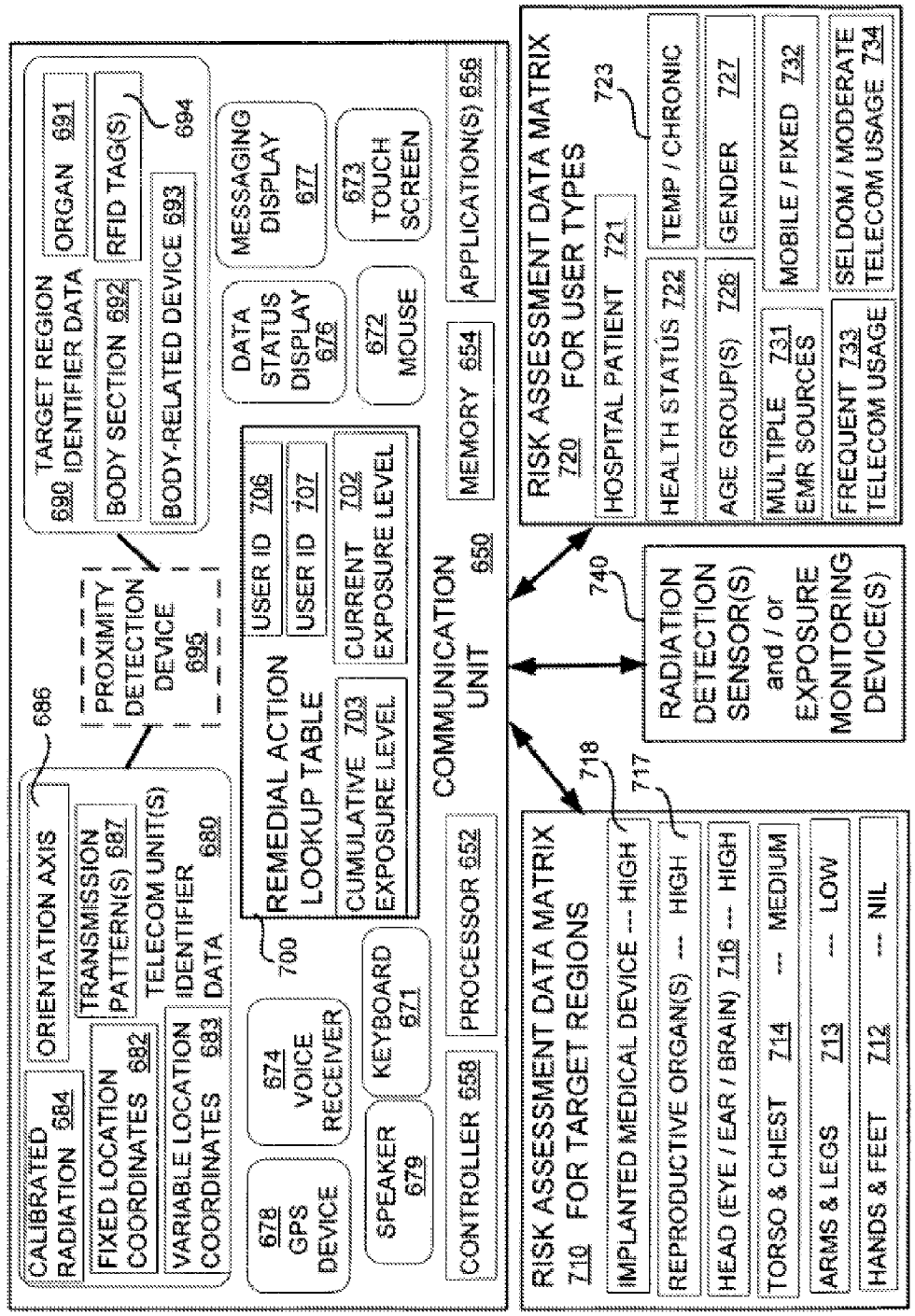
FIG. 14 is a schematic block system diagram for exemplary irradiation protection embodiment features.

Referring to the schematic block diagram of FIG. 14, an exemplary system embodiment for irradiation protection may include communication unit 650 having processor 652, memory 654, one or more program applications 656, and controller 658. The communication unit 650 may be a separate unit or may be incorporated as part of a user's telecom device that generates EMR. Various types of user interfaces may be incorporated in or operably coupled with the communication unit 650 including but not limited to keyboard 671, mouse 672, touch screen 673, voice receiver 674, data/status display 676, messaging display 677, GPS device 678, and speaker 779 to facilitate interactive communications by one or more users associated with the communication module 650.

Various types of updated informational data may be maintained to be accessible to the communication unit 650 including telecom unit(s) identifier data 680, target region identifier data 690, and remedial action lookup table 700. Exemplary telecom unit identifier data 680 may include fixed location coordinates 682, variable location coordinates 683, calibrated radiation 684, orientation axis 686, and transmission pattern(s) 687. Exemplary target region identifier data 690 may include a body organ 691, body section 692, body-related device 693, and one or more radio frequency identification (RFID) tags 694. The exemplary remedial action lookup table may include current exposure level 702, cumulative exposure level 703, first user ID 706, and second user ID 707.

An integral or remote detection module 695 may be operably connected with the target region identifier module 690 and with the telecom location module 680 to enable determination of a separation distance between a particular telecommunication unit and a target body region.

Some exemplary embodiment features may provide a transmission link between the communication unit 650 and as least one radiation detection sensor (see 740) adapted to detect attenuated radiation emissions generated from a telecom unit. Other exemplary embodiment features may provide a transmission link between the communication unit 650 and at least one exposure monitoring device (see 740) adapted to monitor irradiation exposure of a targeted body region.

As illustrated in FIG. 14, the communication unit 650 in some system embodiments may be operably connected with a risk assessment data matrix for target regions 710 wherein some types of bodily-related target regions are deemed to be more vulnerable to electromagnetic irradiation than others. For example, hands and feet may be designated as "nil" risk 712; arms and legs may be designated as "low" risk 713; and torso and chest may be designated as "medium" risk 714. In contrast, sections of the head (e.g., eye, ear, brain) may be designated as "high" risk 716; and reproductive organs may be designated as "high" risk 717. As a further example, a target body region that includes an implanted medical device may be designated as "high" risk 718.

The communication unit 650 in other system embodiments may be operably connected with a risk assessment data matrix for user types 720 wherein some types or categories of people are deemed to be more vulnerable to electromagnetic irradiation than others. For example, different levels of risk assessment may be assigned to a person classified as a hospital patient 721, or a person with a particular health status 722 (e.g. temporary illness or chronic disease 723). As a further example, different levels of risk assessment may be assigned based on one or more age groups 726 or a person's gender 727.

In some situations a different level of risk assessment may be assigned to a person living or working in a place subject to multiple EMR radiation sources 731. Whether the radiation generating device is either mobile or fixed 732 may be a factor in determining an EMR risk assessment. A person in a category of "frequent telecom usage" 733 may be assessed at a higher risk for excessive irradiation exposure than a person in a category of "seldom/moderate telecom usage" 734.

Depending on the circumstances, the various system components including communication unit 650, telecom unit identifier data 680, target region identifier data 690, proximity detection device 695, remedial action lookup table 700, risk assessment data matrices 710, 720 and radiation detection sensors & exposure monitoring devices 740 may be incorporated as part of a user's telecommunication device and/or located externally (e.g., remotely) from such telecommunication device. In some instances certain components may be located at a facility associated with providing irradiation protection services, and/or located in a vehicle or residence or building or workplace of the user. Other locations are possible, and various types of communication links may be provided including but not limited to wireless, cable, satellite, Internet, public networks, private networks, and the like.

It will be further understood from the various embodiment features disclosed herein that certain exemplary data processing functions may be provided by a unitary communication unit 650, and other specified exemplary processing functions may be carried out by separate computerized processing modules.

Figure 15:
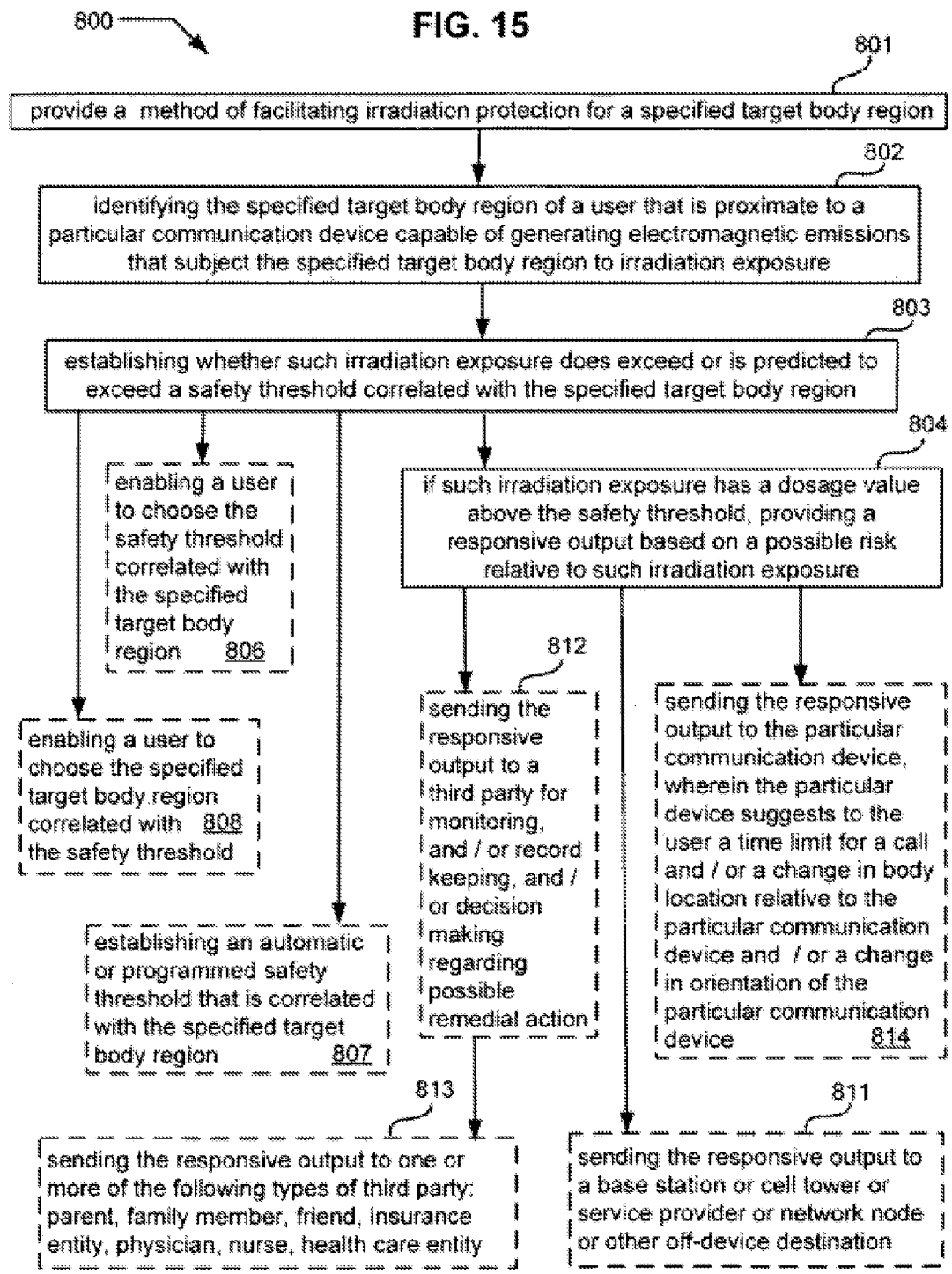
FIG. 15 is a high level flow chart for additional exemplary irradiation protection features.

The high level flow chart of FIG. 15 depicts exemplary embodiment features 800 regarding a method of facilitating irradiation protection for a specified target body region (block 801), wherein the method may include identifying the specified target body region of a user that is proximate to a particular communication device capable of generating electromagnetic emissions that subject the specified target body region to irradiation exposure (block 802); establishing whether such irradiation exposure does exceed or is predicted to exceed a safety threshold correlated with the specified target body region (block 803); and if such irradiation exposure has a dosage value above the safety threshold, providing a responsive output based on a possible risk relative to such irradiation exposure (block 804). Another possible feature may include enabling a user to choose the safety threshold correlated with the specified target body region (block 806).

Additional possible process features may include establishing an automatic or programmed safety threshold that is correlated with the specified target body region (block 807), and enabling a user to choose the specified target body region correlated with the safety threshold (block 808). In some instance exemplary embodiment features may include sending the responsive output to a base station or cell tower or service provider or network node or other off-device destination (block 811). Other possible features may include sending the responsive output to a third party for monitoring, and/or record keeping, and/or decision making regarding possible remedial action (block 812).

Also depicted in FIG. 15 are exemplary aspects that include sending the responsive output to one or more of the following types of third party: parent, family member, friend, insurance entity, physician, nurse, health care entity (block 813). Further possible aspects may include sending the responsive output to the particular communication device, wherein the particular device suggests to the user a time limit for a call and/or a change in body location relative to the particular communication device and/or a change in orientation of the particular communication device (block 814).

Figure 16:
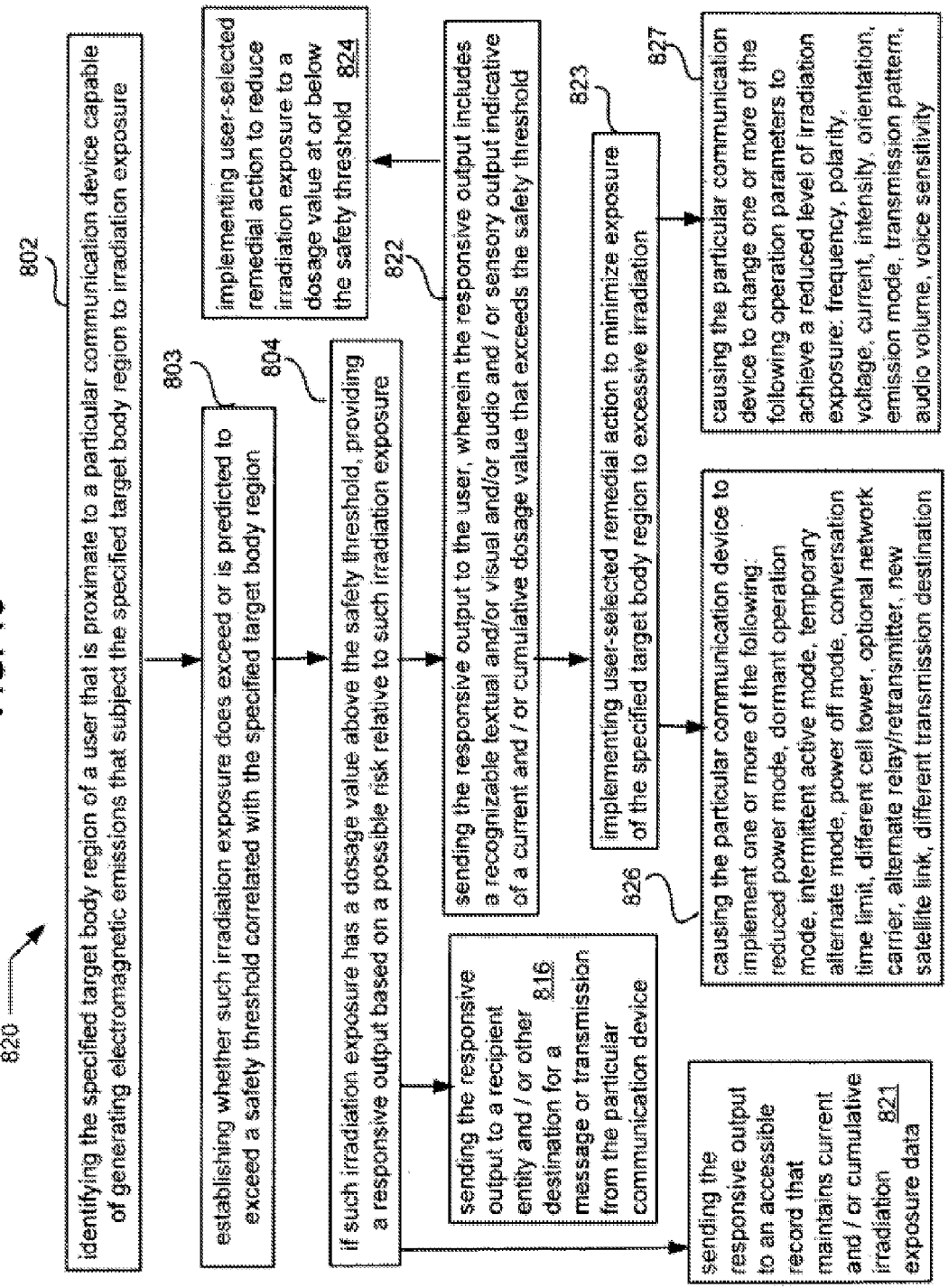

Referring to the flow chart of FIG. 16, various exemplary embodiment features 820 are depicted including previous described aspects 802, 803, 804 along with sending the responsive output to a recipient entity and/or other destination for a message or transmission from the particular communication device (block 816). Additional exemplary features may include sending the responsive output to an accessible record that maintains current and/or cumulative irradiation exposure data (block 821). Other possible process aspects may include sending the responsive output to the user, wherein the responsive output includes a recognizable textual and/or visual and/or audio and/or sensory output indicative of a current and/or cumulative dosage value that exceeds the safety threshold (block 822).

Additional exemplary aspects may include implementing user-selected remedial action to reduce irradiation exposure to a dosage value at or below the safety threshold (block 824), and in some instances may provide for implementing user-selected remedial action to minimize exposure of the specified target body region to excessive irradiation (block 823). Other process aspects may include causing the particular communication device to implement one or more of the following: reduced power mode, dormant operation mode, intermittent active mode, temporary alternate mode, power off mode, conversation time limit, different cell tower, optional network carrier, alternate relay/retransmitter, new satellite link, different transmission destination (block 826). Further exemplary features may include causing the particular communication device to change one or more of the following operation parameters to achieve a reduced level of irradiation exposure: frequency, polarity, voltage, current, intensity, orientation, emission mode, transmission pattern, audio volume, voice sensitivity (block 827).

Various exemplary process features 830 are illustrated in the flow chart of FIG. 17 including previous described features 802, 803, 804 in combination with transmitting the responsive output to a local or remote control module, wherein the responsive output includes a recognizable output signal indicative of a current and/or cumulative dosage value that exceeds the safety threshold (block 832). Additional aspects may include implementing automatic or programmed remedial action to reduce the irradiation exposure to a dosage value at or below the safety threshold (block 834). A further possibility may provide for implementing automatic or programmed remedial action to minimize exposure of the specified target body portion to excessive irradiation (block 833).

Some embodiments may include causing the particular communication device to implement one or more of the following: reduced power mode, dormant operation mode, intermittent active mode, temporary alternate mode, power off mode, conversation time limit, different cell tower, optional network carrier, alternate relay/retransmitter, new satellite link, different transmission destination (block 836). Other embodiments may include causing the particular communication device to change one or more of the following operation parameters to achieve a reduced, level of irradiation exposure: frequency, polarity, voltage, current, intensity, orientation, emission mode, transmission pattern, pulse format, control channel, voice channel, audio volume, voice sensitivity (block 837).

Additional exemplary aspects shown in FIG. 17 regarding target body regions may include identifying one or more of the following types of specified target body-related regions: head, eye, ear, heart, chest, stomach, torso, abdomen, groin, reproductive organ, proximate body surface, vulnerable organ, sensitive body part, cerebral portion, cardio-vascular portion, bionic repair, bionic replacement, implanted medical appliance, therapeutic device, health monitoring apparatus, testing unit, diagnostic component, body accessory (block 839).

Figure 18:
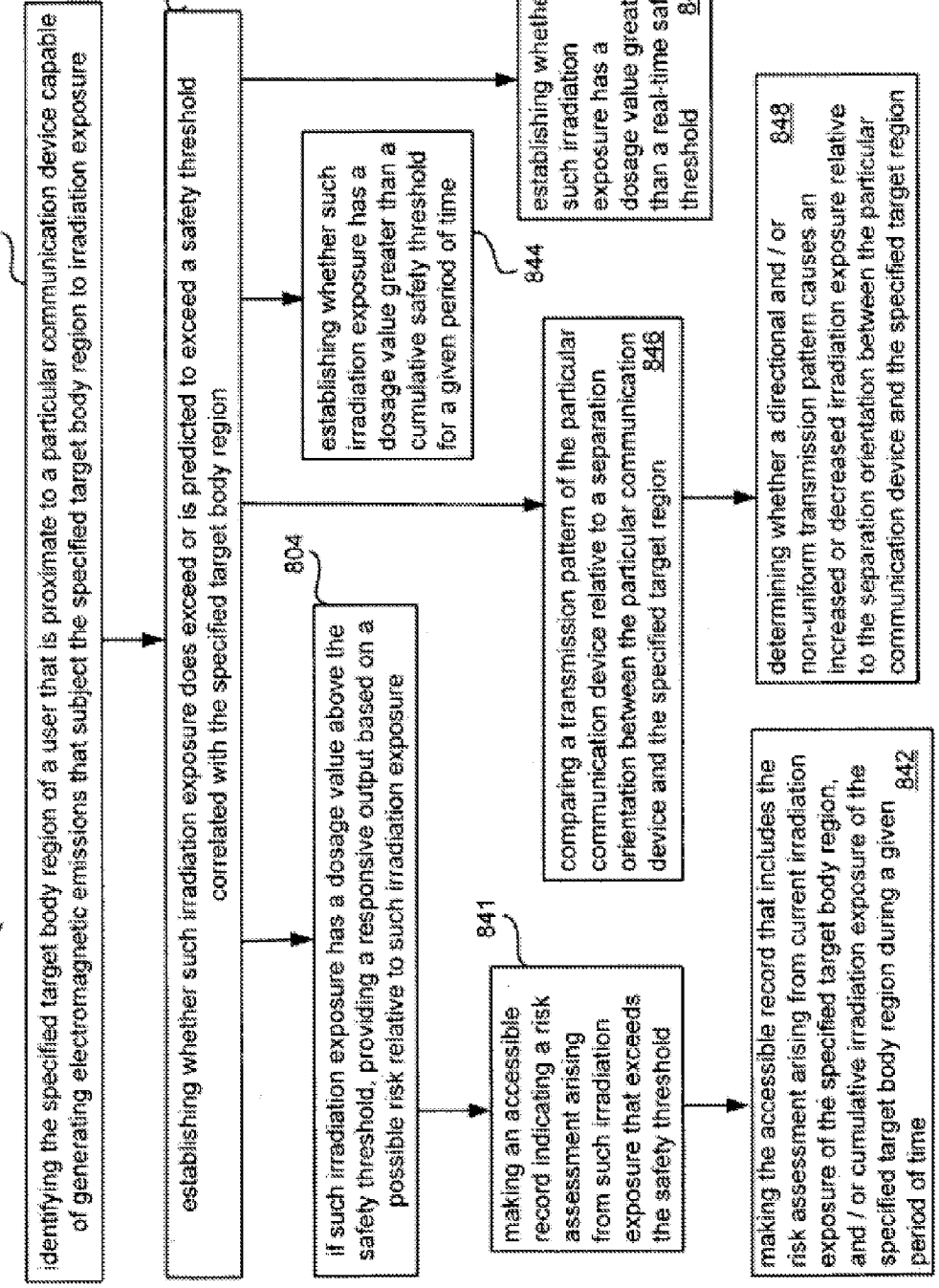

The flow chart of FIG. 18 depicts various exemplary features 840 including previously described features 802, 803, 804 along with making an accessible record indicating a risk assessment arising from such irradiation exposure that exceeds the safety threshold (block 841). Related possibilities may include making the accessible record that includes the risk assessment arising from current irradiation exposure of the specified target body region, and/or cumulative irradiation exposure of the specified target body region during a given period of time (block 842). Further aspects may include establishing whether such irradiation exposure has a dosage value greater than a real-time safety threshold (block 843), and in some instance may further include establishing whether such irradiation exposure has a dosage value greater than a cumulative safety threshold for a given period of time (block 844).

Additional exemplary aspects may include comparing a transmission pattern of the particular communication device relative to a separation orientation between the particular communication device and the specified target region (block 846). Related possible aspects may include determining whether a directional and/or non-uniform transmission pattern causes an increased or decreased irradiation exposure relative to the separation orientation between the particular communication device and the specified target region (block 848).

Figure 19:
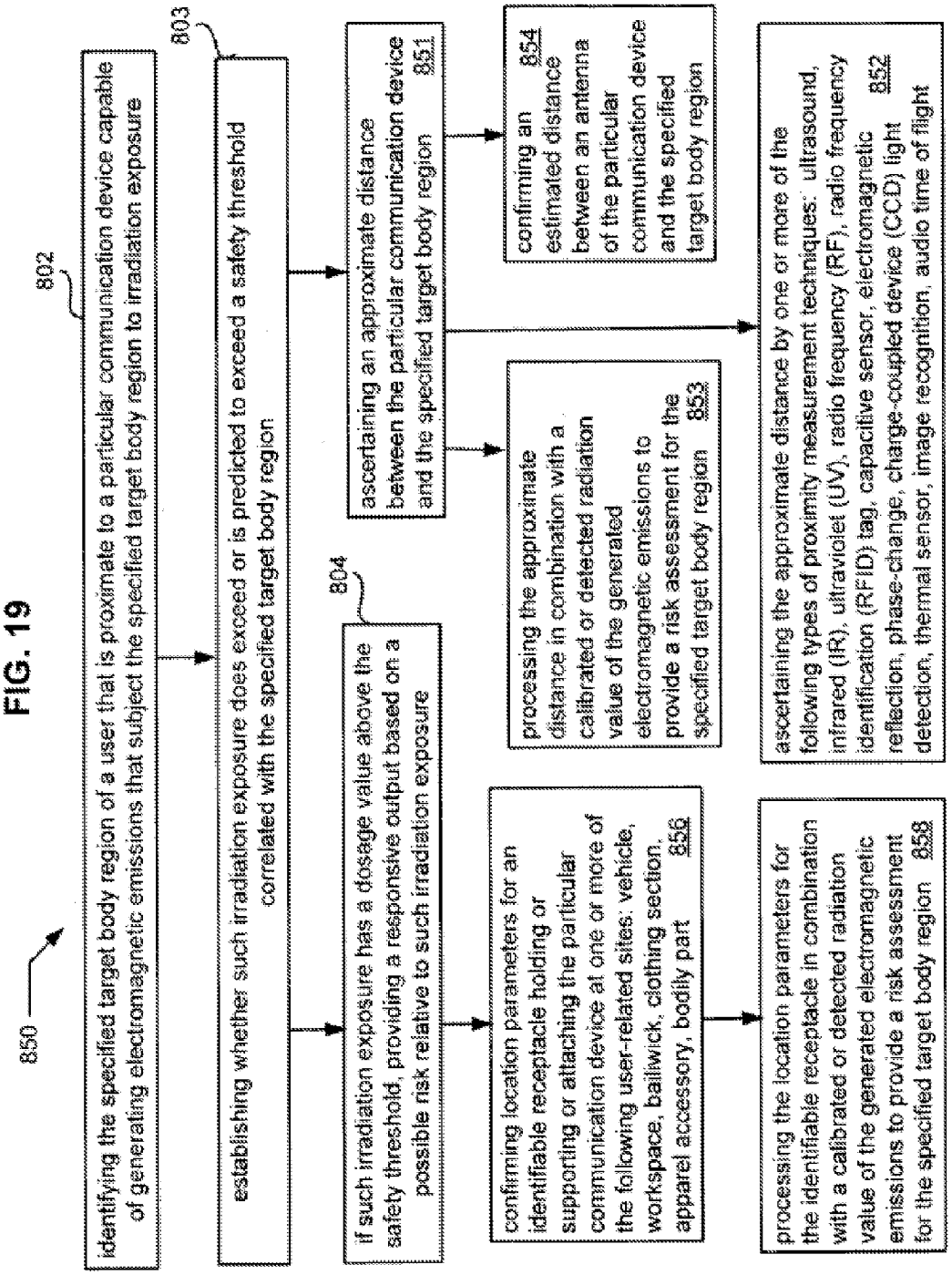

Referring to the exemplary process features 850 shown in the flow chart of FIG. 19, some embodiments may include previously describe aspects 802, 803, 804 in combination with ascertaining an approximate distance between the particular communication device and the specified target body region (block 851). Related process features may include ascertaining the approximate distance by one or more of the following types of proximity measurement techniques: ultrasound, infrared (IR), ultraviolet (UV), radio frequency (RF), radio frequency identification (RFID) tag, capacitive sensor, electromagnetic reflection, phase-change, charge-coupled device (CCD) light detection, thermal sensor, image recognition, audio time of flight (block 852).

Further related process aspects may include processing the approximate distance in combination with a calibrated or detected radiation value of the generated electromagnetic emissions to provide a risk assessment for the specified target body region (block 853). Some embodiments may include confirming an estimated distance between an antenna of the particular communication device and the specified target body region (block 854).

In some instances an exemplary embodiment may include confirming location parameters for an identifiable receptacle holding or supporting or attaching the particular communication device at one or more of the following user-related sites: vehicle, workspace, bailiwick, clothing section, apparel accessory, bodily part (block 856). Further exemplary features may include processing the location parameters for the identifiable receptacle in combination with a calibrated or detected radiation value of the generated electromagnetic emissions to provide a risk assessment for the specified target body region (block 858).

Figure 20:
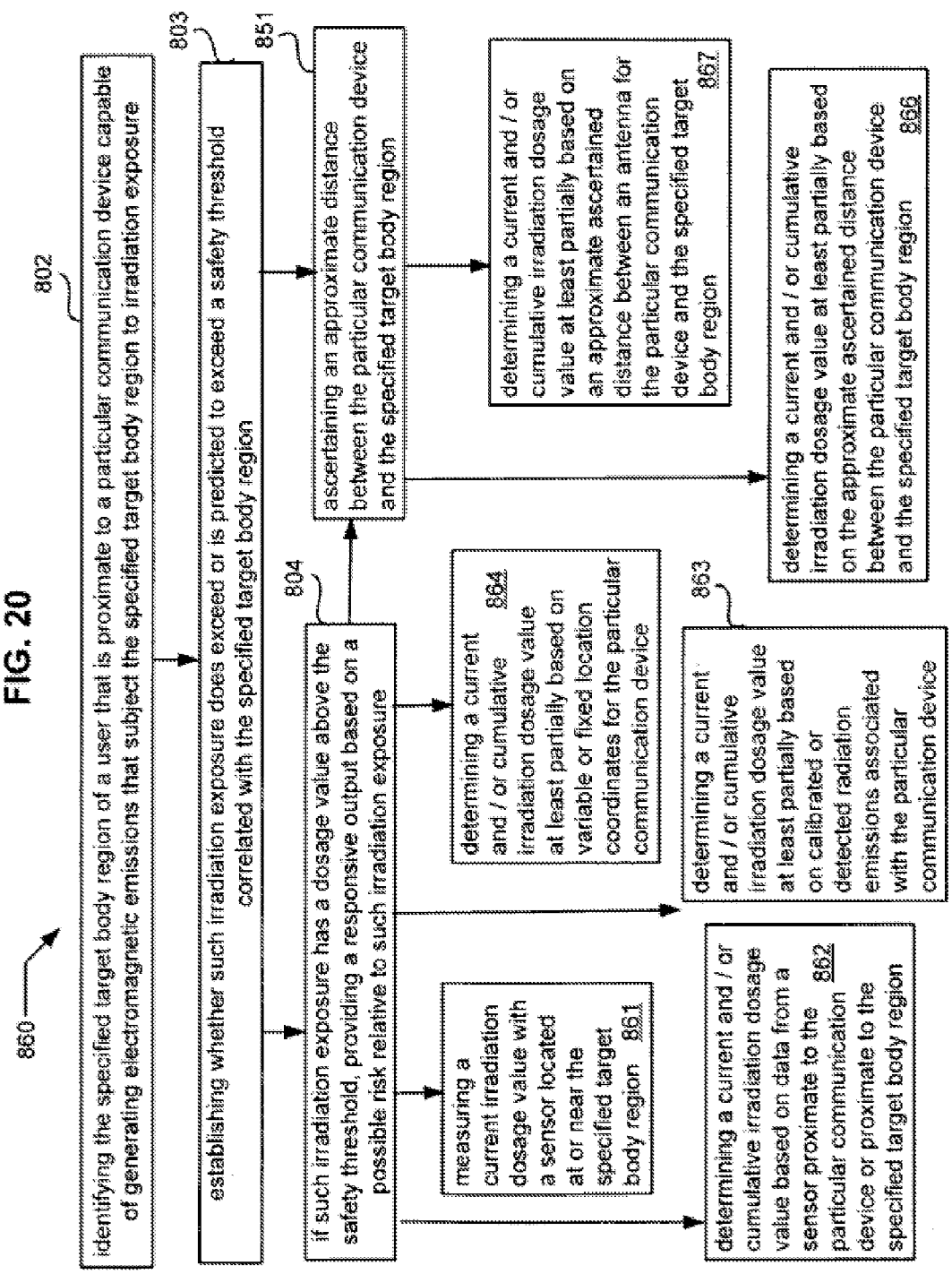

Referring to the flow chart of FIG. 20, possible process features 860 may include previously described aspects 802, 803, 804, 851 as well as determining a current and/or cumulative irradiation dosage value at least partially based on an approximate ascertained distance between the particular communication device and the specified target body region (block 866). In some instances exemplary process features may include determining a current and/or cumulative irradiation dosage value at least partially based on an approximate ascertained distance between an antenna for the particular communication device and the specified target body region (block 867).

Further possible aspects regarding appropriate irradiation exposure dosage values may include measuring a current irradiation dosage value with a sensor located at or near the specified target body region (block 861). Other possible process features may include determining a current and/or cumulative irradiation dosage value based on data from a sensor proximate to the particular communication device or proximate to the specified target body region (block 862).

Some embodiments may include determining a current and/or cumulative irradiation dosage value at least partially based on calibrated or detected radiation emissions associated with the particular communication device (block 863). Other possible embodiment features may include determining a current and/or cumulative irradiation dosage value at least partially based on variable or fixed location coordinates for the particular communication device (block 864). Further related process features (see FIG. 21) may include determining a current and/or cumulative irradiation dosage value at least partially based on an approximate orientation of a transmission pattern of the particular communication device relative to the specified target body region (block 869).

Figure 21:
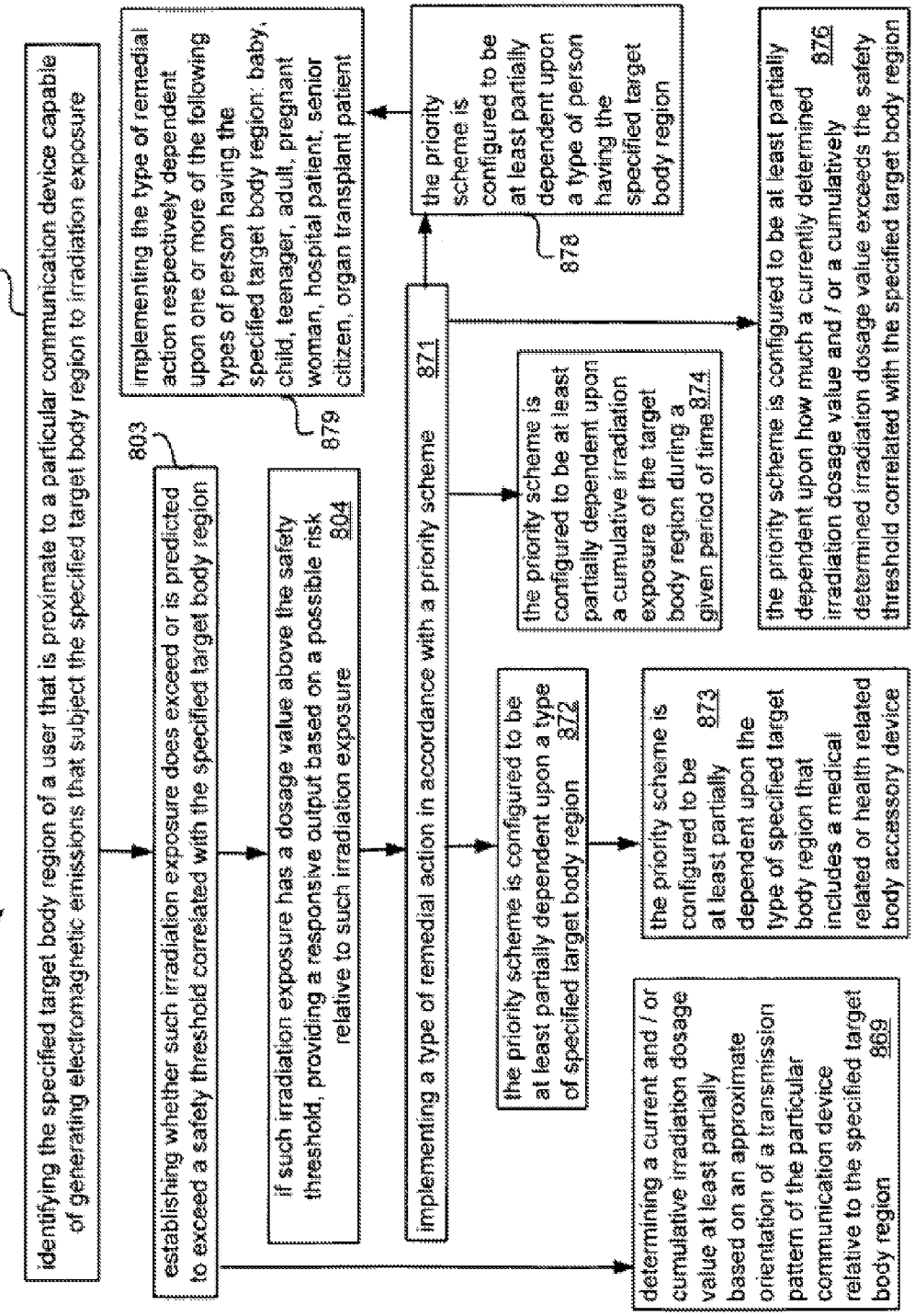

The flow chart of FIG. 21 illustrates additional possible process features 870 including previously described aspects 802, 803, 804 in combination with implementing a type of remedial action accordance with a priority scheme (block 871). Various exemplary priority schemes may be implemented in software and/or circuitry configurations. For example, an exemplary priority scheme may be configured to be implementing a type of remedial action in accordance with a priority scheme configured to be at least partially dependent upon a type of specified target body region (block 872). A related aspect may include implementing the type of remedial action in accordance with the priority scheme configured to be at least partially dependent upon the type of specified target body region that includes a medical related or health related body accessory device (block 873).

Additional embodiment features may include implementing a type of remedial action in accordance with a priority scheme configured to be at least partially dependent upon a cumulative irradiation exposure of the target body region during a given period of time (block 874). In some instances a type of remedial action may be implemented in accordance with a priority scheme configured to be at least partially dependent upon how much a currently determined irradiation dosage value and/or a cumulatively determined irradiation dosage value exceeds the safety threshold correlated with the specified target body region (block 876).

Other possible process aspects may include implementing a type of remedial action accordance with a priority scheme configured to be at least partially dependent upon a type of person having the specified target body region (block 878). For example, an exemplary embodiment may include implementing the type of remedial action respectively dependent upon one or more of the following types of person having the specified target body region: baby, child, teenager, adult, pregnant woman, hospital patient, senior citizen, organ transplant patient (block 879).

Further exemplary aspects 880 are illustrated in FIG. 22, including previously described aspects 802, 803, 804 as well as processing known location coordinates for the particular communication device in combination with a calibrated or detected radiation value of the generated electromatentic emissions to provide a risk assessment for the specified target body region that includes an implanted or attached or user-related body accessory device (block 882). In some instances, exemplary aspects may include confirming fixed or variable location coordinates for one or more of the following types of particular communication device: mobile, hand-held, vehicle-mounted, desktop, head-attached, wrist-attached, hands-free, cell phone, transceiver, transmitter, receiver (block 884).

Exemplary computer program product features 885 depicted in FIG. 23 may include providing computer-readable media having encoded instructions for executing a method of facilitating irradiation protection for a specified target body region (block 886), wherein a possible method may include identifying the specified target body region that is proximate to a particular communication device capable of generating electromagnetic emissions that subject the specified target body region to radiation exposure (block 887), and establishing whether such radiation exposure does exceed or is predicted to exceed a safety threshold correlated with the specified target body region (block 888). Some exemplary embodiments may further include if such radiation exposure has a dosage value above the safety threshold, providing a responsive output based on a possible risk relative to such radiation exposure (block 889).

Other exemplary programmed process features regarding remedial action may include causing the particular communication device to implement one or more of the following: reduced power mode, dormant operation mode, intermittent active mode, temporary alternate mode, power off mode, conversation time limit, different cell tower, optional network carrier, alternate relay/retransmitter, new satellite link, different transmission destination (block 891). Further possible programmed process features regarding remedial action may include causing the particular communication device to change one or more of the following operation parameters to achieve a reduced level of radiation: frequency, polarity, voltage, current, intensity, orientation, emission mode, transmission pattern, audio volume, voice sensitivity (block 892).

Some embodiments may include programmed process features that include confirming location parameters for an identifiable receptacle holding or supporting or attaching the particular communication device at one or more of the following user-related sites: vehicle, workspace, bailiwick, clothing section, apparel accessory, bodily part (block 894). Additional possible programmed process features may include measuring a current irradiation dosage value with a sensor located at or near the specified target body region (block 896). Other exemplary programmed process aspects may include determining a current and/or cumulative irradiation dosage value at least partially based on an approximate orientation of a transmission pattern of the particular communication device relative to the specified target body region (block 897).

It will be understood by those skilled in the art that the various components and elements disclosed in the system and schematic diagrams herein as well as the various steps and sub-steps disclosed in the flow charts herein may be incorporated together in different claimed combinations in order to enhance possible benefits and advantages.

The exemplary system, apparatus, and computer program product embodiments disclosed herein including FIGS. 1-4, FIGS. 13-14 and FIG. 23 along with other components, devices, know-how, skill and techniques known in the art have the capability of implementing and practicing the methods and processes that are depicted in FIGS. 5-12 and 15-22. However it is to be further understood by those skilled in the art that other systems, apparatus and technology may be used to implement and practice such methods and processes.

Exemplary methods, systems and components disclosed herein enable detection and/or monitoring and/or control of electromagnetic radiation (EMR) exposure of target body-related portions of a user operating a telecommunication device. It is understood that some embodiments may include a risk-assessment output that is provided based on a safety threshold or predetermined intrusion level of EMR exposure.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A computer program product comprising non-transitory computer-readable storage media having encoded instructions for executing a method for managing electromagnetic irradiation, wherein the method includes:
   acquiring estimated location parameters for a particular telecommunication device relative to a target body region of a user;
   obtaining a radiation dosage value associated with electromagnetic emissions received at the target body region;
   determining, based on the radiation dosage value, whether the particular telecommunication device is in an active operation mode that generates or is predicted to generate electromagnetic irradiation above a predetermined intrusion level; and
   responsive to confirmation of the determined active operation mode, implementing remedial action to minimize the electromagnetic irradiation of the target body region.

2. The computer program product of claim 1 wherein obtaining the radiation dosage value includes:
   obtaining the radiation dosage value from a sensor proximate to the target body region.

3. The computer program product of claim 1 wherein the method further includes:
   based on the obtained radiation dosage value, providing to the user and/or to a third party a risk assessment of irradiation exposure of one or more of the following types of target body-related regions: head, eye, ear, heart, chest, stomach, torso, abdomen, groin, reproductive organ, proximate body surface, vulnerable organ, sensitive body part, cerebral portion, cardio-vascular portion, bionic repair, bionic replacement, implanted medical appliance, therapeutic device, health monitoring apparatus, testing unit, diagnostic component, body accessory.

4. The computer program product of claim 1 wherein the method further includes:
   obtaining an approximate radiation value for electromagnetic emissions generated from the particular telecommunication device during the active operation mode.

5. The computer program product of claim 4 wherein obtaining the approximate radiation value includes:
   obtaining the approximate radiation value from a calibration table or sensor incorporated with the particular telecommunication device.

6. The computer program product of claim 4 wherein the method further includes:
   processing the approximate radiation value in combination with the estimated location parameters to provide a risk assessment arising from such exposure of the target body region.

7. The computer program product of claim 6 wherein the method further includes:
   providing the risk assessment based on a currently generated radiation value for the electromagnetic emissions of the particular telecommunication device.

8. The computer program product of claim 6 wherein the method further includes:
   providing the risk assessment based on a cumulative record of electromagnetic emissions of the particular telecommunication device during a given time period.

9. The computer program product of claim 6 wherein the method further includes:
   providing the risk assessment based on user-specified criteria.

10. The computer program product of claim 6 wherein the method further includes:
    making an accessible data record indicating the risk assessment arising from such exposure of the target body region.

11. The computer program product of claim 6 wherein the method further includes:
    providing to the user or to a third party an indication of the risk assessment.

12. The computer program product of claim 6 wherein the method further includes:
    providing to the user a visual or audio or haptic indicator of the risk assessment.

13. The computer program product of claim 6 wherein the method further includes:
    advising one or more current conversation recipients of the risk assessment.

14. The computer program product of claim 1 wherein implementing remedial action includes:
    causing the particular telecommunication device to change to a reduced power mode or dormant operation mode.

15. The computer program product of claim 1 wherein implementing remedial action includes:
    causing the particular telecommunication device to change to a different operation mode configured to generate radiation emissions at or below the predetermined intrusion level.

16. The computer program product of claim 1 wherein implementing remedial action includes:
    changing a transmission pattern of the particular telecommunication device for sending and/or receiving messages.

17. The computer program product of claim 1 wherein the method further includes:
    providing a time limit for the user and a recipient to finish a conversation.

18. The computer program product of claim 1 wherein the method further includes:
    switching to a different communication relay or cell tower or network carrier or retransmitter or satellite.

19. The computer program product of claim 1 wherein implementing remedial action includes:
    increasing an audio volume or voice sensitivity of the particular telecommunication device to facilitate greater separation between the particular telecommunication device and a user's head.

20. The computer program product of claim 1 wherein implementing remedial action includes:
    increasing an audio volume during listening mode and/or increasing a voice sensitivity during speaking mode, for the particular telecommunication device.

21. The computer program product of claim 1 wherein implementing remedial action includes:
    suggesting to a user an orientation change of the particular telecommunication device relative to the target body region.

22. The computer program product of claim 1 wherein implementing remedial action includes:
   suggesting to a user a location change of the particular telecommunication device relative to the target body region.

23. The computer program product of claim 1 wherein implementing remedial action includes:
   causing a change in location and/or orientation of the particular telecommunication device.

24. The computer program product of claim 1 wherein implementing remedial action includes:
   causing the particular telecommunication device to operate intermittently or temporarily in the active operation mode that generates radiation emissions above the predetermined intrusion level.

25. The computer program product of claim 1 wherein implementing remedial action includes:
   causing the particular telecommunication device to change one or more of the following operation parameters to achieve a reduced intrusion level: frequency, polarity, voltage, current, intensity, orientation, emission mode, transmission patter, audio volume, voice sensitivity.

26. The computer program product of claim 1 wherein the method further includes:
   communicating an output identifier indicative of currently and/or cumulatively generated radiation emissions above the predetermined intrusion level.

27. The computer program product of claim 26 wherein communicating the output identifier includes:
   providing to the user a recognizable textual and/or visual and/or audio and/or sensory output indicative of currently and/or cumulatively generated radiation emissions above the predetermined intrusion level.

28. The computer program product of claim 27 wherein implementing remedial action includes:
   implementing user-selected remedial action to minimize exposure of the target body region to excessive electromagnetic emissions received from the particular telecommunication device.

29. The computer program product of claim 26 wherein communicating the output identifier includes:
   transmitting to a control module a recognizable output signal indicative of currently and/or cumulatively generated radiation emissions above the predetermined intrusion level.

30. The computer program product of claim 29 wherein implementing remedial action includes:
   responsive to said transmitted recognizable output signal, implementing automatic or programmed consequential action by the control module operable to minimize exposure of the target body region to excessive electromagnetic emissions received from the particular telecommunication device.

31. The computer program product of claim 1 wherein acquiring estimated location parameters for the particular telecommunication device includes:
   ascertaining a separation distance between the particular telecommunication device and the target body region.

32. The computer program product of claim 31 wherein said method further includes:
   processing an obtained radiation value for electromagnetic emissions generated from the particular telecommunication device in combination with the separation distance between the particular telecommunication device and the target body region to provide a risk assessment arising from such exposure of the target body region.

33. The computer program product of claim 31 wherein ascertaining the separation distance between the particular telecommunication device and the target body region includes:
   ascertaining the separation distance between an omni-directional or internal antenna of the particular telecommunication device and the target body region.

34. The computer program product of claim 31 wherein ascertaining the separation distance between the particular telecommunication device and the target body region includes:
   ascertaining the separation distance between a directional or external antenna of the particular telecommunication device and the target body region.

35. The computer program product of claim 31 wherein ascertaining the separation distance between the particular telecommunication device and the target body region includes:
   ascertaining the separation distance by processing data obtained by one or more of the following types of proximity measurement and/or location detection techniques: ultrasound, infrared (IR), ultraviolet (UV), radio frequency (RF), radio frequency identification (RFID) tag, capacitive sensor, electromagnetic reflection, phase-change, charge-coupled device (CCD) light detection, thermal sensor, image recognition, audio time of flight.

36. The computer program product of claim 1 wherein the method further includes:
   confirming an orientation factor for separation between the particular telecommunication device and the target body region, which orientation factor is determined relative to a transmission pattern of the particular telecommunication device.

37. The computer program product of claim 36 wherein the method further includes:
   processing an obtained radiation value for electromagnetic emissions generated from the particular telecommunication device in combination with the orientation factor to provide a risk assessment arising from such exposure of the target body region.

38. The computer program product of claim 37 wherein the method further includes:
   indicating a first risk assessment if the orientation factor is deemed relatively insignificant due to a uniform transmission pattern of the particular telecommunication device.

39. The computer program product of claim 37 wherein the method further includes:
   indicating a second risk assessment at least partially based on a significant orientation factor due to a non-uniform and/or directional transmission pattern of the particular telecommunication device.

40. The computer program product of claim 1 wherein acquiring the estimated location parameters for the particular telecommunication device includes:
   establishing location parameters for an identifiable receptacle holding the particular telecommunication device proximate to the target body region.

41. The computer program product of claim 40 wherein establishing location parameters for the identifiable receptacle includes:
   establishing location parameters for the identifiable receptacle attached directly or indirectly to a known bodily location of the user.

42. The computer program product of claim 40 wherein establishing location parameters for the identifiable receptacle includes:
  establishing location parameters for the identifiable receptacle attached or supported or held at a known location in a vehicle of the user.

43. The computer program product of claim 40 wherein establishing location parameters for the identifiable receptacle includes:
  establishing location parameters for the identifiable receptacle attached or supported or held at a known location in a workspace or bailiwick of the user.

44. The computer program product of claim 1 wherein acquiring the estimated location parameters for the particular telecommunication device includes:
  establishing location parameters for an identifiable clothing section or apparel accessory attaching or supporting or holding the particular telecommunication device proximate to the target body region.

45. The computer program product of claim 1 wherein acquiring the estimated parameters for the particular telecommunication device includes:
  establishing location parameters for the particular telecommunication device attached or supported or held at a known location relative to the user.

46. The computer program product of claim 1 wherein acquiring the estimated location parameters for the particular telecommunication device includes:
  establishing location parameters for one or more of the following types of telecommunication device: mobile, hand-held, vehicle-mounted, desktop, head-attached, wrist-attached, hands-free, cell phone, transceiver, transmitter, receiver.

47. The computer program product of claim 1 wherein method acquiring the estimated location parameters for the particular telecommunication device includes:
  establishing location coordinates for the particular telecommunication device relative to a medical or health related body accessory device subject to irradiation exposure.

48. The computer program product of claim 1 wherein implementing remedial action includes:
  implementing the remedial action to minimize exposure of one or more of the following types of target body-related regions to excessive electromagnetic emissions: head, eye, ear, heart, chest, stomach, torso, abdomen, groin, reproductive organ, proximate body surface, vulnerable organ, sensitive body part, cerebral portion, cardio-vascular portion, bionic repair, bionic replacement, implanted medical appliance, therapeutic device, health monitoring apparatus, testing unit, diagnostic component, body accessory.

49. The computer program product of claim 1 wherein the method further includes:
  establishing the predetermined intrusion level based on a type of implanted or attached or user-related body accessory device to be protected from excessive electromagnetic emissions.

50. The computer program product of claim 1 wherein the method further includes:
  establishing the predetermined intrusion level based on a type of target body region to be protected from excessive electromagnetic emissions.

51. The computer program product of claim 1 wherein the method further includes:
  establishing the predetermined intrusion level based on a type or category of user to be protected from excessive electromagnetic emissions.

52. The computer program product of claim 1 wherein implementing remedial action to minimize electromagnetic irradiation exposure includes:
  implementing automatic or programmed consequential remedial action with respect to exposure of the target body region to attenuated electromagnetic emissions received from the particular telecommunication device.

53. The computer program product of claim 1 wherein implementing remedial action to minimize electromagnetic irradiation exposure includes:
  implementing user-selective remedial action with respect to exposure of the target body region to attenuated electromagnetic emissions received from the particular telecommunication device.

54. A system for managing electromagnetic irradiation from a telecommunication device comprising:
  proximity determination means for acquiring estimated location parameters for a particular telecommunication device relative to a target body region of a user;
  radiation detection means for obtaining a radiation dosage value associated with electromagnetic emissions received at the target body region;
  monitoring means for determining, based on the radiation dosage value, whether the particular telecommunication device is in an active operation mode that generates or is predicted to generate electromagnetic irradiation above a predetermined intrusion level; and
  control module means configured to be responsive to confirmation of the determined active operation mode in order to implement consequential or selective remedial action with respect to exposure of the target body region to attenuated electromagnetic emissions received from the particular telecommunication device.

* * * * *

UNITED STATES PATENT AND TRADEMARK OFFICE
CERTIFICATE OF CORRECTION

| | | |
|---|---|---|
| PATENT NO. | : 8,463,288 B2 | Page 1 of 1 |
| APPLICATION NO. | : 12/803143 | |
| DATED | : June 11, 2013 | |
| INVENTOR(S) | : Hyde et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 434 days.

Signed and Sealed this
Twenty-first Day of January, 2014

Michelle K. Lee
*Deputy Director of the United States Patent and Trademark Office*